(12) United States Patent
Lee

(10) Patent No.: US 8,987,425 B2
(45) Date of Patent: Mar. 24, 2015

(54) PHARMACEUTICAL COMPOSITION FOR PREVENTING OR TREATING CANCER

(75) Inventor: Jae-il Lee, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 13/557,891

(22) Filed: Jul. 25, 2012

(65) Prior Publication Data

US 2013/0108639 A1    May 2, 2013

(30) Foreign Application Priority Data

Jul. 25, 2011    (KR) ........................ 10-2011-0073635

(51) Int. Cl.
| | |
|---|---|
| C07K 16/00 | (2006.01) |
| C07K 16/46 | (2006.01) |
| C07K 16/28 | (2006.01) |
| C07K 16/18 | (2006.01) |

(52) U.S. Cl.
CPC ........... *C07K 16/468* (2013.01); *C07K 16/2809* (2013.01); *C07K 16/18* (2013.01); *C07K 16/46* (2013.01); *C07K 2319/00* (2013.01)
USPC ................... 530/391.1; 530/391.7; 530/391.9

(58) Field of Classification Search
None
See application file for complete search history.

(56) References Cited

U.S. PATENT DOCUMENTS

| | | |
|---|---|---|
| 7,323,171 B2 | 1/2008 | Wallner et al. |
| 2003/0232399 A1 | 12/2003 | Robertson et al. |
| 2005/0113297 A1 | 5/2005 | Francois et al. |
| 2005/0143886 A1 | 6/2005 | Theisen |
| 2006/0024315 A1 | 2/2006 | Schnitzer et al. |
| 2007/0122414 A1 | 5/2007 | Georges et al. |
| 2007/0134687 A1 | 6/2007 | Georges et al. |
| 2008/0213256 A1* | 9/2008 | Kufer et al. ................. 424/133.1 |
| 2012/0251453 A1* | 10/2012 | Fukuda et al. ................. 424/9.1 |

FOREIGN PATENT DOCUMENTS

| | | |
|---|---|---|
| EP | 1336620 A1 | 8/2003 |
| WO | WO 93/23537 A1 | 11/1993 |
| WO | 00/39283 A1 | 7/2000 |
| WO | WO2004106380 A2 * | 12/2004 |
| WO | WO 2005/117848 A2 | 12/2005 |
| WO | WO 2006/130525 A2 | 12/2006 |
| WO | WO 2011/079304 A1 | 6/2011 |

OTHER PUBLICATIONS

Wolf et al. BiTEs: bispecific antibody constructs with unique anti-tumor activity. Drug Discov Today 2005;10:1237-44.*
Falini et al. (2004) Simple diagnostic assay for hairy cell leukaemia by immunocytochemical detection of annexin A1 (ANXA1). Lancet 363, 1869-1870.*
Aina et al. Therapeutic cancer targeting peptides. Biopolymers. 2002;66(3): 184-99.*
Lu X et al Preferential antagonism of the interactions of the integrin alpha lib beta 3 with immobilized glycoprotein ligands by snake-venom RGD (Arg-Gly-Asp) proteins. Evidence supporting a functional role for the amino acid residues flanking the tripeptide RGD in determining the inhibitory properties of snake-venom . . . (1994) Biochem J 304:929-936.*
Suntharalingam et al. Cytokine storm in a phase 1 trial of the anti-CD28 monoclonal antibody TGN1412. N Engl J Med. 355(10): 1018-28, 2006.*
Bai et al. Overexpression of annexin 1 in pancreatic cancer and its clinical significance. World J Gastroenterol 2004;10(10):1466-1470.*
Kvansakul et al. EMBO J 2004, 23:1223-1233.*
Cole et al., *Molecular Immunology*, 45: 2700-2709 (2008).
Oh et al., "Subtractive Proteomic Mapping of the Endothelial Surface in Lung and Solid Tumours for Tissue-Specific Therapy," *Nature*, 429: 629-635 (2004).
Hammond et al., "Selective Targeting and Potent Control of Tumor Growth using an EphA2/CD3-Biospecific Single-Chain Antibody Construct," *Cancer Res*, 67(8): 3927-3935 (2007).
Fukuda et al., "Targeted Drug Delivery to Tumor Vasculature by a Carbohydrate-Mimicry Peptide," *The 2009 NCI Translational Science Meeting*, Nov. 5-7, 2009, Vienna, VA—Abstract Book: 209 (2009).
Kufer et al., "A Revival of Bispecific Antibodies," *Trends in Biotech*, 22(5): 238-244 (2004).
Pameijer et al., "Conversion of a Tumor-Binding Peptide Identified by Phage Display to a Functional Chimeric T-Cell Antigen Receptor," *Molecular Therapy*, 13(1): S104 (2006).
Kuroki et al., "Re-Targeting of Cytotoxic T Lymphocytes and/or Natural Killer Cells to CEA-Expressing Tumor Cells with Anti-CEA Antibody Activity," *Anticancer Research*, 3725-3732 (2005).
Hatakeyama et al., "Targeted Drug Delivery to Tumor Vasculature by a Carbohydrate Mimetic Peptide," *PNAS*, 108(49): 19587-19592 (2011).
Extended European Search Report by the European Patent Office in Application No. 12177837.7, mailed on Oct. 10, 2012.
Löffler et al., "A recombinant bispecific single-chain antibody, CD19 X CD3, includes rapid and high lymphoma-directed cytotoxicity by unstimulated T lymphocytes," *Blood*, 95 (6), 2098-2103 (2000).
Carver et al., "Caveolae: Mining Little Caves for New Cancer Targets", *Nature Reviews/Cancer*, 3, 571-581 (2003).
Dreifer et al., "Extremely Potent, Rapid and Costimulation-Independent Cytotoxic T-Cell Response Against Lymphoma Cells Catalyzed by a Single-Chain Bispecific Antibody", *Int. J. Cancer*,100, 690-697 (2002).
Oh et al., "Subtractive proteomic mapping of the endothelial surface in lung and solid tumours for tissue-specific therapy", *Nature*, 429, 629-635 (2004).

* cited by examiner

*Primary Examiner* — Maher Haddad
(74) *Attorney, Agent, or Firm* — Leydig, Voit & Mayer, Ltd.

(57) ABSTRACT

The invention provides a fusion protein comprising (a) a first protein comprising a polypeptide which specifically binds to Annexin A1 and (b) a second protein comprising a polypeptide which induces a cytotoxic activity of a cytotoxic lymphocyte, pharmaceutical compositions comprising the fusion protein, and methods of treating or preventing cancer by administering the pharmaceutical compositions.

3 Claims, 3 Drawing Sheets

PHARMACEUTICAL COMPOSITION FOR PREVENTING OR TREATING CANCER

CROSS-REFERENCE TO RELATED APPLICATION

This application claims the benefit of Korean Patent Application No. 10-2011-0073635, filed on Jul. 25, 2011, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 69,093 Byte ASCII (Text) file named "708782ST25.TXT," created Dec. 26, 2012.

BACKGROUND OF THE INVENTION

Currently, the development of antibodies for treatment is being actively conducted. This provides a solution to diseases which are difficult to treat with existing synthetic drugs, and is replacing synthetic drugs. Presently, 16 antibodies for treatment are commercially available, and about 7000 or more antibodies are under development by about 300 or more companies worldwide. These antibody products are continuously growing the pharmaceutical market.

Angiogenesis is essential for cell differentiation in all cancer tissues, and no single therapeutic agent has been available due to its low efficiency even though a target for inhibition of angiogenesis is already known. In addition, a therapeutic agent, which may be widely used on various kinds of cancers, has not been yet developed.

A protein, called lipocortin, calpactin, endonexin, and the like twenty years ago, was given the standardized name Annexin, which has been used for the past decade.

Annexin binds to calcium and phospholipid, and has a uniquely conserved domain in which about 70 amino acid sequences including the 'GXGTDE' (SEQ ID NO: 118) motif called endonexin fold are repeated four times (sometimes repeated eight times). Annexins, which are conventionally known, include a conserved domain. Proteins are identified as annexin proteins depending on whether the sequence is conserved or not. The annexin protein is known to be present in various living organisms from mammals to molds, and it has been reported that Annexins I, II, III, IV, V, VI, VII, VIII, XIII, and the like are found in humans. The annexin protein is known to be involved in the structural formation of bone and in various biological phenomena, such as membrane trafficking, transmembrane channel activity, inhibition of phospholipase A2, coagulation inhibition, transduction of mitogen signals, and mediation of cell-matrix interaction.

Although the related art discloses a method of delivering materials by using antibodies binding to Annexin A1, there is no disclosure about cancer treatments by using antibodies. Although another related art discloses a method of treating cancer by combining inhibitors against multi-markers of cancer, the use of Annexin A1 as a marker is not disclosed.

BRIEF SUMMARY OF THE INVENTION

The invention provides a fusion protein comprising (a) a first protein comprising a polypeptide which specifically binds to Annexin A1 and (b) a second protein comprising a polypeptide which induces a cytotoxic activity of a cytotoxic lymphocyte, as well as pharmaceutical compositions comprising the fusion protein and a pharmaceutically acceptable carrier and method of treating or preventing cancer using the inventive pharmaceutical compositions.

Additional aspects will be set forth in part in the description which follows and, in part, will be apparent from the description, or may be learned by practice of the presented embodiments.

DETAILED DESCRIPTION OF THE INVENTION

Figure 1:
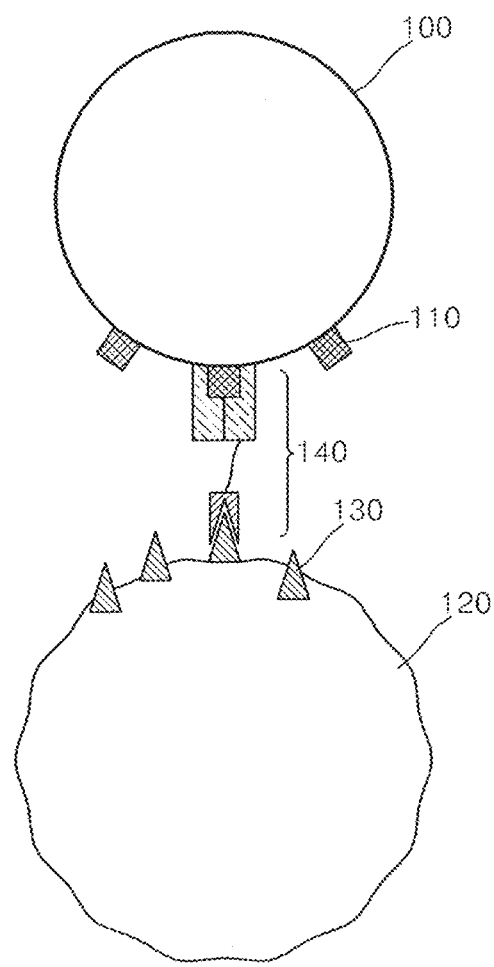
FIG. 1 is a schematic view illustrating a fusion protein comprising a first protein including a polypeptide which specifically binds to Annexin A1 and a second protein including a polypeptide which induces a cytotoxic activity of a cytotoxic lymphocyte that acts on a cancer cell.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

The inventors discovered that fusion proteins comprising (a) a first protein comprising a polypeptide that specifically binds to Annexin A1 and (b) a second protein comprising a polypeptide that induces cytotoxic activity of a cytotoxic lymphocyte can be used to target cancer cells that express Annexin A1 on the surface of the cells.

Accordingly, the invention provides a fusion protein comprising, consisting essentially of, or consisting of (a) a first protein comprising a polypeptide that specifically binds to Annexin A1 and (b) a second protein comprising a polypeptide that induces cytotoxic activity of a cytotoxic lymphocyte.

The invention also provides a pharmaceutical composition comprising a fusion protein comprising (a) a first protein comprising a polypeptide which specifically binds to Annexin A1 and a second protein comprising a polypeptide which induces a cytotoxic activity of a cytotoxic lymphocyte; and a pharmaceutically acceptable carrier.

As used herein, the term "fusion protein" refers to a protein complex including two or more (e.g., three, four, five, or more) proteins and which is formed by chemical combination of the two or more proteins of themselves or combination through a linker.

Annexin, one of targets to which the fusion protein specifically binds, is known to be present in various living organisms from mammals to molds, and has a uniquely conserved domain in which about 70 amino acid sequences including the 'GXGTDE' (SEQ ID NO: 118) motif called endonexin fold are repeated four times (sometimes repeated eight times). Annexin is known to be involved in various biological phenomena, such as membrane trafficking, transmembrane channel activity, inhibition of phospholipase A2, coagulation inhibition, transduction of mitogen signals, and mediation of cell-matrix interaction.

Annexin A1, a subfamily of Annexin, also is known as lipocortin I. Annexin A1 belongs to the Annexin family of $Ca^{2+}$-dependent phospholipid-binding proteins and may be located on the cytosolic face of the plasma membrane. Annexin A1 protein can be encoded by the ANXA1 gene and/or have a molecular mass of about 40 kDa with phospholipase A2 inhibitory activity. In addition, Annexin A1 may be used as a marker for cancer because it has characteristics to be positioned in a normal cell and migrate to the outer membrane of the cell as a result of production of cancer. Thus, a first protein including a polypeptide which specifically binds to Annexin A1 in the fusion protein may specifically bind to Annexin A1 on the surface of cancer cells through the polypeptide.

As used herein, the term "specifically bind(s) or specifically binding" is identical to the meaning known to those skilled in the art, and refers to a specific interaction between molecules by a covalent bond or non-covalent bond between two or more polypeptides or proteins. For example, the concept that an antigen specifically interacts with an antibody to cause an immunological reaction may be included.

As used herein, the term "polypeptide" refers to a linear molecule formed by amino acid residues bound to each other through a peptide bond. The polypeptide which specifically binds to Annexin A1 may have, for example, 4 to 200 (e.g., 5, 10, 20, 30, 40, 50, 60, 70, 80, 90, 100, 110, 120, 130, 140, 150, 160, 170, 180, and 190), 4 to 100, or 4 to 50 amino acid residues. The polypeptide with less than 4 amino acid residues may have low binding affinity to Annexin A1. The polypeptide with more than 200 amino acid residues may not specifically bind to Annexin A1. The polypeptide may be prepared by various methods known in the art, for example, gene cloning method and solid phase synthesis technique. In addition, the polypeptide may be empirically obtained by a commercially available polypeptide library (for example, a polypeptide library, a bacteriophage M13-polypeptide library, and the like).

According to an embodiment, the first protein may be a full-length antibody or an antigen binding fragment thereof. The full-length antibody has a structure with two full-length light chains and two full-length heavy chains, and each light chain is linked to each heavy chain by a disulfide bond (SS-bond). A constant region of the antibody is divided into a heavy chain constant region and a light chain variable region, and the heavy chain variable region has gamma (γ), mu (μ), alpha (α), delta (δ), and epsilon (ε) types and gamma1 (γ1), gamma2 (γ2), gamma3 (γ3), gamma4 (γ4), alpha1 (α1), and alpha2 (α2) subclasses. The light chain constant region has kappa (κ) and lambda (λ) types.

The antibody includes, but not limited to, a monoclonal antibody, a bispecific antibody, a non-human antibody, a human antibody, a humanized antibody, a chimeric antibody, a single chain Fv (scFv), a Fab fragment, a F(ab') fragment, a disulfide-bond Fv (sdFV), an anti-idiotype (anti-Id) antibody, and an epitope-binding fragment thereof.

The antibody may be a humanized antibody or a human antibody. A non-human, for example, a humanized antibody of mouse may be a chimeric immunoglobulin including a minimum sequence derived from an immunoglobulin of mouse, an immunoglobulin chain or a fragment thereof, for example, Fv, Fab, Fab', F(ab')$_2$, or other antigen-binding subsequences of antibodies.

Methods of humanizing non-human antibodies are well known in the art. Generally, humanized antibodies have one or more amino acid residues introduced from a non-human supply source. Humanization may be performed by essentially substituting complementary determining regions (CDRs) or portions of CDR sequences of a rodent with sequences corresponding to human antibodies. Accordingly, a region smaller than a variable region of a substantially intact human antibody may be substituted by a corresponding sequence from a non-human species. For example, humanized antibodies may be those in which some CDR residues and possibly some framework (FR) residues are substituted by residues from similar sites in antibodies of a rodent.

The human antibody refers to an antibody in which variable and constant region sequences of heavy and light chains are derived from humans, and may be produced by using various techniques, such as genetic recombinant techniques and genetic engineering.

Effector parts of human antibodies may interact with other parts of the human immune system. In addition, the human immune system does not recognize human antibodies as foreign materials, and thus, the immune reaction against antibodies introduced into a living human body may be significantly less severe than that against wholly foreign non-human or partially foreign chimeric antibodies. Moreover, human antibodies introduced into a living human body have a half-life substantially identical to that of naturally occurring human antibodies, and therefore, dosage and frequency of administration may be reduced. As used herein, the term "chimeric" refers to an antibody or antigen-binding site including sequences derived from two different species.

As used herein, the term "antigen binding fragment" refers to a fragment of the whole structure of an immunoglobulin to which an antigen may bind. For example, the antigen binding fragment may be a F(ab')$_2$ fragment, a Fab' fragment, a Fab fragment, a Fv fragment, or a scFv fragment, but is not limited thereto. Among the antigen-binding fragments, the Fab fragment contains variable regions of light and heavy chains, a constant region of a light chain, and a first constant region ($C_{H1}$) of a heavy chain. The Fab fragment has one antigen binding site. The Fab' fragment is different from a Fab fragment in that Fab' has a hinge region with at least one cysteine residue at the C-terminal end of the heavy chain $C_{H1}$ domain. The F(ab')$_2$ antibody is produced with cysteine residues at the hinge region forming a disulfide bond. The Fv fragment is a minimum antibody fragment which contains only a heavy chain variable site and a light chain variable site, and recombinant techniques for producing the Fv fragment are well-known in the art. Two-chain Fv fragments may have a structure in which the heavy chain and light chain variable regions are linked by a non-covalent bond, and single-chain Fv (scFv) fragments may have a dimer structure in which the heavy chain and light chain variable regions are covalently bound via a peptide linker, or are directly linked to each other at the C-terminus. The antigen binding fragment may be obtained by using a protease (for example, the whole antibody may be digested by papain to obtain Fab fragments or by pepsin to obtain F(ab')$_2$ fragments), and the antigen binding fragment may be prepared by a genetic recombinant technique.

According to an embodiment, the first protein of the fusion protein may be a polypeptide having an amino acid sequence represented by $X_1$-Trp-Gly-His-$X_2$-$X_3$-Trp (SEQ ID NO: 119), wherein $X_1$ and $X_2$ are independently an amino acid selected from the group consisting of Ala, Ile, Leu, Met, Phe, Pro, Trp, Val, Asn, Cys, Gln, Gly, Ser, Thr, Tyr, Asp, Glu, Arg, His, and Lys, and $X_3$ is an amino acid selected from the group consisting of Ala, Ile, Leu, Met, Phe, Pro, Trp, Val, Asn, Cys, Gln, Gly, Ser, Thr, and Tyr. The polypeptide having the amino acid sequence represented by $X_1$-Trp-Gly-His-$X_2$-$X_3$-Trp (SEQ ID NO: 119) may be selected from the group consisting of amino acid sequences of SEQ ID NOS: 1 to 8.

According to an embodiment, the first protein, which specifically binds to Annexin A1, may be selected from polypeptides having an amino acid sequence of SEQ ID NOS: 9 to 42. These may not be a polypeptide having an amino acid sequence represented by $X_1$-Trp-Gly-His-$X_2$-$X_3$-Trp (SEQ ID NO: 119).

According to an embodiment, the second protein may specifically bind to a surface marker of the cytotoxic lymphocyte. For example, the surface marker may be selected from, but not limited to, CD2, CD3, CD4, CD5, CD7, CD8, CD16, CD28, CD56, CD57, and TCR.

According to an embodiment, the second protein may be a polypeptide having an amino acid sequence of SEQ ID NO: 116 or SEQ ID NO: 117. SEQ ID NO: 116 is an amino acid sequence comprising $V_H$ and $V_L$ of mouse anti-CD3, and SEQ ID NO: 117 is an amino acid sequence comprising $V_H$ and $V_L$ of human anti-CD3.

According to an embodiment, the second protein may be a full-length antibody or an antigen binding fragment thereof. The full-length antibody or the antigen-binding fragment thereof is described as above.

The antibody or the antigen-binding fragment thereof may include a variant that retains the ability to specifically recognize Annexin A1 or a surface marker of a cytotoxic lymphocyte. For example, modification may be made to the amino acid sequence of an antibody in order to improve the binding affinity of the antibody and/or other biological properties. This modification includes, for example, a deletion, insertion, and/or substitution of amino acid sequence residues of the antibody. This amino acid modification is based on the relative similarity of an amino acid side-chain substituent, for example, properties such as hydrophobicity, hydrophilicity, charge, size, and the like. For example, arginine (Arg), lysine (Lys), and histidine (His) are all positively-charged residues, alanine (Ala), glycine (Gly), and serine (Ser) are all a similar size, and phenylalanine (Phe), tryptophan (Trp) and tyrosine (Tyr) all have a generally similar shape. Therefore, based upon these considerations, Arg, Lys and His; Ala, Gly and Ser; and Phe, Trp and Tyr may be biologically functional equivalents.

Amino acid substitutions in proteins which do not generally alter the activity of such molecules are known in the art. The most commonly occurring exchanges are: Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. In consideration of a modification having the biologically equivalent activity, it can be understood that the antibody or the antigen-binding fragment thereof, which specifically binds to a surface marker of Annexin A1 or a cytotoxic lymphocyte, may also include a sequence exhibiting a substantial identity to a sequence described in the Sequence Listing. The substantial identity may be a sequence showing at least 60% identity, at least 70% identity, at least 80% identity, or at least 90% identity (e.g., at least 95% identity or at least 99% identity) when an alignment is made to maximally correspond an amino acid sequence of the Sequence Listing to any other sequence and an aligned sequence is analyzed by using an algorithm typically used in the art. Alignment methods for comparison of sequences are known in the art. For example, a sequence analysis program such as blastp, blastx, tblastn, and tblastx may be used on Internet through the NCBI Basic Local Alignment Search Tool (BLAST).

According to an embodiment, the fusion protein optionally can include a linker which joins the first protein with the second protein. Suitable linkers for use in the invention are known in the art and include peptide linkers (e.g., consisting of a plurality of amino acid residues). The fusion protein can comprise no linker or one or more (e.g., two, three, four, or more) linkers of any suitable length as long as the biological activity of the fusion protein is not affected. In one embodiment, the linker has 10 amino acids or less (e.g., 9, 8, 7, 6, 5, 4, 3, 2, or 1 amino acids).

While not wishing to be bound by any particular theory, the peptide linker may allow each protein of the fusion protein to be folded into appropriate secondary and tertiary structures by separating the first protein including a polypeptide which specifically binds to Annexin A1 from the second protein including the polypeptide which induces an activity of a cytotoxic lymphocyte at a sufficient distance. For example, the peptide linker may include Gly, Asn, and Ser residues, and neutral amino acids, such as Thr and Ala. An amino acid sequence appropriate for the peptide linker is known in the art, and may be, for example, $Gly_4$-Ser (SEQ ID NO: 120), $(Gly_4$-$Ser)_3$ (SEQ ID NO: 121), or $Gly_4$-Ser-$Gly_5$-Ser (SEQ ID NO: 122).

The peptide linker may be linked to the N- and/or the C-terminal region of the polypeptide which specifically binds to Annexin A1. In particular, when the peptide linker is linked to the N-terminus and C-terminus of the polypeptide, the peptide linker may include each cysteine, and a disulfide bond may occur between each cysteine to allow the polypeptide to be present between the two cysteines.

The fusion protein optionally comprises other components, such as chemotherapeutic agents, toxins, affinity tags (e.g., a FLAG-tag, His-tag, HA-tag, and myc-tag), signal sequence (e.g., pelB periplasmic signal sequence) and the like.

The invention also provides a method for treating or preventing cancer of a subject comprising administering to the subject a pharmaceutical composition comprising a fusion protein comprising, consisting essentially of, or consisting of (a) a first protein including a polypeptide which specifically binds to a pharmaceutically effective amount of Annexin A1 and (b) a second protein including a polypeptide which induces a cytotoxic activity of a cytotoxic lymphocyte and a pharmaceutically acceptable carrier, such that cancer in the subject is treated or prevented.

Cancer which may be prevented or treated by the composition comprising the fusion protein may be selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, pancreatic cancer, glioblastoma, cervical cancer, ovarian cancer, bladder cancer, hepatic tumor, breast cancer, colon cancer, large intestine cancer, endometrial carcinoma or uterine carcinoma, salivary gland tumor, kidney cancer, liver cancer, prostate cancer, vulvar cancer, thyroid cancer, and head and neck cancer, but it is not limited thereto.

The composition treats or prevents the cancer by binding Annexin on the surface of a cancer cell and binding to a surface marker (e.g., CD3) on the surface of a cytotoxic lymphocyte. While not wishing to be bound by any particular theory, it is believed that the composition treats or prevents cancer by positioning a cyotoxic lymphocyte near the cancer cell, which cancer cell subsequently is destroyed by the cytotoxic granules secreted by the cytotoxic lymphocyte.

As illustrated by FIG. 1, the fusion protein 140 comprises a first protein including a polypeptide which specifically binds to Annexin A1 and a second protein including a polypeptide which induces a cytotoxic activity of a cytotoxic lymphocyte that acts on a cancer cell 120. The fusion protein 140 specifically binds both to Annexin 130 on the surface of the cancer cell 120 and to a surface marker 110 on the surface of a cytotoxic lymphocyte 100. By positioning the cytotoxic lymphocyte 100 around the cancer cell 120, the cancer cell 120 can be specifically killed through cytotoxic granules which the cytotoxic lymphocyte 100 secretes without affecting normal cells. Thus, the inventive fusion protein (e.g., in a pharmaceutical composition) specifically targets cancer cells for destruction without affecting normal (non-cancerous) cells.

The pharmaceutically acceptable carrier included in the composition is commonly used in formulation, and may include, but not limited to, lactose, dextrose, sucrose, sorbitol, mannitol, starch, gum acacia, calcium phosphate, alginates, gelatin, calcium silicate, microcrystalline cellulose, polyvinylpyrrolidone, cellulose, water, syrup, methyl cellulose, methylhydroxy benzoate, propylhydroxy benzoate, talc, magnesium stearate, and mineral oil. The pharmaceutical composition may additionally include a lubricant, a wetting agent, a sweetener, a flavor enhancer, an emulsifying agent, a suspension agent, a preservative, and the like besides the ingredients.

The composition for preventing or treating cancer may be administered orally or parenterally. Parenteral administration may include intravenous injection, subcutaneous injection, muscular injection, intraperitoneal injection, endothelial administration, local administration, intranasal administration, intrapulmonary administration, and rectal administration. Since oral administration leads to digestion of protein or peptide, an active agent may be coated or formulated in a pharmaceutical composition to protect the composition from decomposition in the stomach. In addition, the composition may be administered by any apparatus with targeting ability to home to specific cells.

A suitable dosage of the composition for preventing or treating cancer may depend on many factors, such as formulation methods, administration methods, patient age, body weight, gender, pathologic conditions, diets, administration time, administration route, excretion speed, and reaction sensitivity. A dose of the composition may be in the range of about 0.001 to about 100 mg/kg for an adult. As used herein, the term "therapeutically effective amount" refers to a sufficient amount used in preventing or treating cancer.

The composition may be formulated with a pharmaceutically acceptable carrier and/or an excipient into a unit dosage form or a multiple dosage form by any method known to those skilled in the art. The formulation may be a solution, a suspension, a syrup, or an emulsion in oil or an aqueous medium, an extract, pulvis, powder, granules, a tablet, or a capsule, and may additionally include a dispersing agent or a stabilizing agent. In addition, the composition may be administered as an individual therapeutic, or in combination with other therapeutics, and may be administered sequentially or simultaneously with conventional therapeutics.

The composition may include an antibody or antigen binding fragments thereof, and thus, may be formulated as an immunoliposome. The liposome including the antibody may be prepared using any method well known in the art. The immunoliposome is a lipid composition including phosphatidylcholine, cholesterol, and polyethyleneglycol-derived phosphatidylethanolamine, and may be prepared, for example, by a reverse phase evaporation method. For example, F(ab')$_2$ fragments of the antibody may be attached to the liposome through a disulfide exchange reaction.

A subject to which the pharmaceutical composition for preventing or treating cancer may be administered includes all animals. For example, the subject may be a human or an animal such as a dog, a cat, a rodent (e.g., a mouse, rat, guinea pig, or hamster), and a primate except for a human.

According to another aspect of the present invention, a method for preparing the fusion protein includes culturing a cell including a polynucleotide sequence encoding a fusion protein comprising, consisting essentially of, or consisting of a first protein comprising a polypeptide which specifically binds to Annexin A1 and a second protein comprising a polypeptide which induces a cytotoxic activity of a cytotoxic lymphocyte (e.g., wherein the second protein can be linked to the end of the first protein); and obtaining a protein expressed from a culture produced in the culturing of the cell.

The culturing of a transformed cell may be performed by various methods known in the art. For example, a protein secreted in vivo or in vitro may be obtained by inoculating a transformed cell into an YT liquid phase medium to perform a culturing, adding an IPTG to the medium at a time point when the cell density reaches a certain level to induce the expression of a protein by a lacZ promoter, and culturing the protein.

The protein secreted in vivo or in vitro may be obtained in a purified form by various purification methods known in the art. For example, a protein may be obtained in a purified form through a purification method, such as a solubility fractionation by ammonium sulfate, and size classification and filtration and various chromatography separation methods (manufactured for separation according to size, hydrophobicity, or hydrophilicity). For example, when a fusion protein is fused to a GST and a 6×His, a desired protein may be easily obtained by using a resin column to which glutathione is bound and a $Ni^{2+}$-NTA His-binding resin column, respectively.

EXAMPLES

The following examples further illustrate the invention but, of course, should not be construed as in any way limiting its scope.

Example 1

Screening of a Polypeptide which Specifically Binds to Annexin A1

(1) Bio-Panning

The polynucleotides encoding Annexin A1 were chemically synthesized by Genotech, Inc. and used to express Annexin A1 for isolation and purification. Annexin A1 was immobilized onto a plate, to which a phage display polypeptide library (Dyax Corp.) was added for binding, and a polypeptide expression phage which binds with a high affinity was selected through various binding times and washing conditions.

A bead panning method was used as the panning Specifically, magnetic beads with streptavidin immobilized on their surface were mixed with Annexin A1 to which biotin was conjugated, and the mixture was stirred at 4° C. for 18 hrs to immobilize the protein on the bead surface. Magnetic beads on which the protein was immobilized were blocked at room temperature for 2 hrs with skim milk, and then a phage solution displaying a polypeptide on the surface of the bead was added. The resulting product was stirred for 2 hrs for reaction and washed with a PBS solution (1.06 mM $KH_2PO_4$, 155.17 mM NaCl, and 2.97 mM $Na_2HPO_4\text{-}7H_2O$) and a PBS solution including 0.1% Tween 20. Only a phage that bound to the antigen was separated. The panning process was performed two or three times according to the number of phages obtained after panning.

(2) Identification of a Sequence of a Polypeptide which Specifically Binds to a Phage ELISA and Annexin A1

Phage clones obtained in the panning process were each infected with *E. coli* XL1-Blue, and cultured at about 37° C. for 14 hrs to obtain a phage solution. Annexin A1 was added to a 96-well microtiter plate (Nunc, Inc.), and allowed to stand at about 4° C. for 18 hrs to immobilize the protein on the plate surface. The plate on which the protein was immobilized was blocked at room temperature for 1 hr with skim milk, and then 100 μL of the phage solution was added. The phage was allowed to react with the protein at room temperature for 2 hrs, and the mixture was washed with the PBS solution including 0.1% Tween 20. Subsequently, an anti-M13 antibody (GE Healthcare) with which HRP specifically reacting with the phage was conjugated was added to the mixture for reaction at room temperature for 1 hr, and then washed twice with the PBS solution including 0.1% Tween 20. Finally, 100 μL of a trimethylbenzidine (TMB) substrate (Sigma) was added to each well of the plate to induce a color reaction. Subsequently 50 μL of 5 N $H_2SO_4$ solution was added to stop the reaction, and then the $OD_{450}$ values were measured with a plate reader (Molecular Devices).

As a result, 42 phage clones in total were identified that had a high reactivity with Annexin A1. Colony PCR was performed using a primer set (SEQ ID NO: 114 and SEQ ID NO: 115) for identification of a nucleotide sequence of the polypeptide which specifically binds to Annexin A1 from single clones of the phages. PCR was performed by using a GeneAmp PCR System 9700 (Applied Biosystem) with PCR conditions as follows: at 94° C. for 5 min; 30 times repetition of a continuous reaction at 94° C. for 1 min, at 60° C. for 1 min, and at 72° C. for 1.5 min; at 72° C. for 10 min; and cooling at 4° C. Subsequently, a washing and sequence analysis (Solgent) of polynucleotide fragments obtained from the solution was performed, and a sequence of the polypeptide which specifically binds to Annexin A1 was identified (Table 1). Table 1 identifies the portion of a polypeptide displayed on the phage (not including the linker), that is, an amino acid sequence of a polypeptide which specifically binds to Annexin A1 and the corresponding nucleic acid sequence.

TABLE 1

| Number | Amino acid sequence | Nucleic Acid Sequence |
|---|---|---|
| 1 | QWGHTLW (SEQ ID NO: 1) | cagtggggccataccctgtgg (SEQ ID NO: 43) |
| 2 | KWGHEVW (SEQ ID NO: 2) | aaatggggccatgaagtgtgg (SEQ ID NO: 44) |
| 3 | WWGHEQW (SEQ ID NO: 3) | tggtggggccatgaacagtgg (SEQ ID NO: 45) |
| 4 | PWGHEIW (SEQ ID NO: 4) | ccgtggggccatgaaatttgg (SEQ ID NO: 46) |
| 5 | LWGHHIW (SEQ ID NO: 5) | ctgtggggccatcatatttgg (SEQ ID NO: 47) |
| 6 | LWGHQIW (SEQ ID NO: 6) | ctgtggggccatcagatttgg (SEQ ID NO: 48) |
| 7 | LWGHGMW (SEQ ID NO: 7) | ctgtggggccatggcatgtgg (SEQ ID NO: 49) |
| 8 | AWGHPFW (SEQ ID NO: 8) | gcgtggggccatccgttttgg (SEQ ID NO: 50) |
| 9 | MNRV (SEQ ID NO: 9) | atgaaccgcgtg (SEQ ID NO: 51) |
| 10 | SLNSIL (SEQ ID NO: 10) | agcctgaacagcattctg (SEQ ID NO: 52) |
| 11 | NLNAWF (SEQ ID NO: 11) | aacctgaacgcgtggttt (SEQ ID NO: 53) |
| 12 | VEWPWW (SEQ ID NO: 12) | gtggaatggccgtggtgg (SEQ ID NO: 54) |
| 13 | WLWPRL (SEQ ID NO: 13) | tggctgtggccgcgcctg (SEQ ID NO: 55) |
| 14 | IDYGLF (SEQ ID NO: 14) | attgattatggcctgttt (SEQ ID NO: 56) |
| 15 | VEGQQWW (SEQ ID NO: 15) | gtggaaggccagcagtggtgg (SEQ ID NO: 57) |
| 16 | WMGHSAW (SEQ ID NO: 16) | tggatgggccatagcgcgtgg (SEQ ID NO: 58) |
| 17 | GIHHPIW (SEQ ID NO: 17) | ggcattcatcatccgatttgg (SEQ ID NO: 59) |
| 18 | WGGHPIW (SEQ ID NO: 18) | tggggcggccatccgatttgg (SEQ ID NO: 60) |
| 19 | PWAKIFW (SEQ ID NO: 19) | ccgtgggcgaaaattttttgg (SEQ ID NO: 61) |
| 20 | MGSKMWG (SEQ ID NO: 20) | atgggcagcaaaatgtgggc (SEQ ID NO: 62) |
| 21 | MLWEDQD (SEQ ID NO: 21) | atgctgtgggaagatcaggat (SEQ ID NO: 63) |
| 22 | ELFDGYD (SEQ ID NO: 22) | gaactgtttgatggctatgat (SEQ ID NO: 64) |
| 23 | WPWEANH (SEQ ID NO: 23) | tggccgtgggaagcgaaccat (SEQ ID NO: 65) |
| 24 | EQYGFPF (SEQ ID NO: 24) | gaacagtatggctttccgttt (SEQ ID NO: 66) |

TABLE 1-continued

| Number | Amino acid sequence | Nucleic Acid Sequence |
|---|---|---|
| 25 | SGFGHMIW (SEQ ID NO: 25) | agcggctttggccatatgatttgg (SEQ ID NO: 67) |
| 26 | ETRFHAIW (SEQ ID NO: 26) | gaaacccgctttcatgcgatttgg (SEQ ID NO: 68) |
| 27 | MLHHHQRE (SEQ ID NO: 27) | atgctgcatcatcatcagcgcgaa (SEQ ID NO: 69) |
| 28 | ALHNEPHT (SEQ ID NO: 28) | gcgctgcataacgaaccgcatacc (SEQ ID NO: 70) |
| 29 | AFHNDPAE (SEQ ID NO: 29) | gcgtttcataacgatccggcggaa (SEQ ID NO: 71) |
| 30 | LLFSDIGN (SEQ ID NO: 30) | ctgctgtttagcgatattggcaac (SEQ ID NO: 72) |
| 31 | LVLKGKWH (SEQ ID NO: 31) | ctggtgctgaaaggcaaatggcat (SEQ ID NO: 73) |
| 32 | SGNGKPFWM (SEQ ID NO: 32) | agcggcaacggcaaaccgttttggatg (SEQ ID NO: 74) |
| 33 | IQRGGVDWS (SEQ ID NO: 33) | attcagcgcggcggcgtggattggagc (SEQ ID NO: 75) |
| 34 | RDSQSWSWS (SEQ ID NO: 34) | cgcgatagccagagctggagctggagc (SEQ ID NO: 76) |
| 35 | LLESQNPQD (SEQ ID NO: 35) | ctgctggaaagccagaacccgcaggat (SEQ ID NO: 77) |
| 36 | IINGWNPIW (SEQ ID NO: 36) | attattaacggctggaacccgatttgg (SEQ ID NO: 78) |
| 37 | DWTTAYGPS (SEQ ID NO: 37) | gattggaccaccgcgtatggcccgagc (SEQ ID NO: 79) |
| 38 | IYDGNWSYWH (SEQ ID NO: 38) | atttatgatggcaactggagctattggcat (SEQ ID NO: 80) |
| 39 | STDSNWFFNA (SEQ ID NO: 39) | agcaccgatagcaactggttttttaacgcg (SEQ ID NO: 81) |
| 40 | MPENWISWYR (SEQ ID NO: 40) | atgccggaaaactggattagctggtatcgc (SEQ ID NO: 82) |
| 41 | VRTDWYSMLM (SEQ ID NO: 41) | gtgcgcaccgattggtatagcatgctgatg (SEQ ID NO: 83) |
| 42 | MIQTSSANRD (SEQ ID NO: 42) | atgattcagaccagcagcgcgaaccgcgat (SEQ ID NO: 84) |

Example 2

Figure 2:
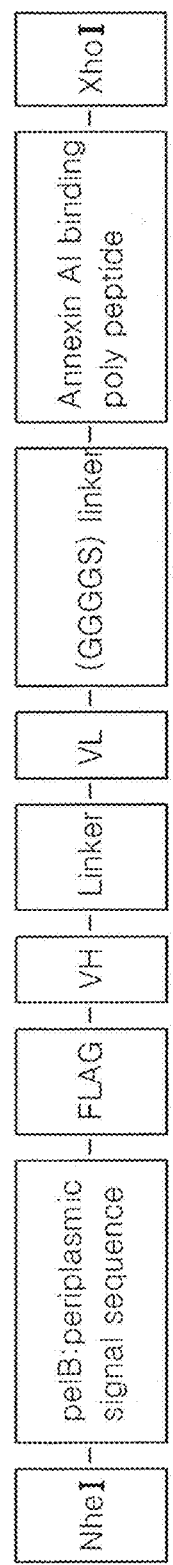
FIG. 2 is a schematic view of a NdeI-XhoI fragment which is inserted into a vector for expression of a fusion protein consisting of a first protein including a polypeptide which specifically binds to Annexin A1 and a second protein including a polypeptide which induces a cytotoxic activity of a cytotoxic lymphocyte according to an embodiment. The (GGGGS) linker corresponds to SEQ ID NO: 120.

Preparation of an Expression Vector of a Fusion Protein Consisting of an Anti-CD3 and Annexin A1 Binding Polypeptide In the present Example, an expression vector for production of a fusion protein comprising (a) an anti-CD3 polypeptide which may specifically bind to CD3 (a polypeptide which induces a cytotoxic activity of a cytotoxic lymphocyte) and (b) the Annexin A1 binding polypeptide prepared in the Example 1 was prepared. NheI-XhoI fragments including a structure as shown in FIG. 2 were chemically synthesized by Genotech, Inc., and the synthesized NheI-XhoI fragments were digested with NheI and XhoI and inserted into pET21b (Promega) digested with the same restriction enzyme to complete an expression vector. The NheI-XhoI fragment was manufactured into 16 types in total by combining 2 types (mouse or human) of polynucleotides encoding the anti-CD3 and 8 types of polynucleotides encoding an Annexin A1 binding polypeptide (SEQ ID NO: 8, SEQ ID NO: 5, SEQ ID NO: 21, SEQ ID NO: 19, SEQ ID NO: 4, SEQ ID NO: 1, SEQ ID NO: 15, and SEQ ID NO: 16, respectively). Each of the NheI-XhoI fragments was represented by SEQ ID NOS: 85 to 100. The fusion proteins which were expressed from the NheI-XhoI fragments were designated as M1, M2, M3, M4, M5, M6, M7, M8, H1, H2, H3, H4, H5, H6, H7 and H8, respectively.

In addition, in order to improve the solubility of a fusion protein expressed, a vector for expression of a protein with ubiquitin attached to the fusion protein was manufactured by using the expression vector. The ubiquitin was allowed to be positioned between pelB and FLAG in the NheI-XhoI fragment shown in FIG. 2. A method for manufacturing a vector for expression of the fusion protein to which ubiquitin was attached was as follows.

First, PCR was performed using the expression vector as a template, a forward primer (5'-cgc catatgaaatacctgctgccgaccgctg-3' (pelB:NdeI-F; SEQ ID NO: 101)) designed to include a NdeI restriction site and include the 5' region of pelB, and a reverse primer (5'-cccggatccggc-catgccggctggg-3' (pelB-NcoI:BamHI-R; SEQ ID NO: 102)) designed to include a BamHI restriction site and include the 3' region of pelB. The PCR product obtained was digested with NdeI and BamHI, and purified to obtain NdeI-BamHI fragments.

Subsequently, a vector including a polynucleotide (SEQ ID NO: 103) encoding ubiquitin between BamHI of the pET21b vector and EcoRI restriction site was digested with NdeI and BamHI and purified, and the NdeI-BamHI fragment was subjected to ligation. The ligation product was sequenced and identified.

Subsequently, DNA fragments including a polynucleotide encoding a FLAG-VH-linker-VL-(GGGGS)linker (SEQ ID NO: 120)-Annexin A1 binding polypeptide were obtained by PCR using each of the 16 types of expression vectors as a template and the following forward and reverse primers. The forward primer was designed by including a EcoRI restriction site and a FLAG tag, and using a part corresponding to the VH of a mouse anti-CD3 antibody and a part corresponding to the VH of a human anti-CD3 antibody each differently. The reverse primer was designed to include a XhoI restriction site and include some of a polynucleotide encoding an Annexin A1 binding polypeptide. The primers used are as follows:

Forward primers:

(SEQ ID NO: 104)
5'-ccggaattcgactacaaagatgatgacgataaggatatcaaac-3'
(Flag-mouse_a-CD3: EcoRI-F)

(SEQ ID NO: 105)
5'-ccggaattcgactacaaagatgatgacgataaggagctg-3'
(Flag-human_a-CD3: EcoRI-F)

Reverse primers:

(SEQ ID NO: 106)
5'-ccgctcgaggcaccaaaacggatgg-3'
(pep1: XhoI-R)

(SEQ ID NO: 107)
5'-ccgctcgaggcaccaaatatgatggcc-3'
(pep2: XhoI-R)

(SEQ ID NO: 108)
5'-ccgctcgaggcaatcctgatcttcccac-3'
(pep3: XhoI-R)

(SEQ ID NO: 109)
5'-ccgctcgaggcaccaaaaaatttcgc-3'
(pep4: XhoI-R)

(SEQ ID NO: 110)
5'-ccgctcgaggcaccaaatttcatgacc-3'
(pep5: XhoI-R)

(SEQ ID NO: 111)
5'-ccgctcgaggcaccacagggtatgacc-3'
(pep6: XhoI-R)

(SEQ ID NO: 112)
5'-ccgctcgaggcaccaccactgctgg-3'
(pep7: XhoI-R)

(SEQ ID NO: 113)
5'-ccgctcgaggcaccacgcggaatg-3'
(pep8: XhoI-R)

Subsequently, the obtained PCR products were digested with EcoRI and XhoI and purified, and the ligation product was also digested with EcoRI and XhoI and purified. The purified products were ligated with each other, sequenced, and identified. Proteins with ubiquitin attached to the fusion proteins were designated as Ub-M1, Ub-M2, Ub-M3, Ub-M4, Ub-M5, Ub-M6, Ub-M7, Ub-M8, Ub-H1, Ub-H2, Ub-H3, Ub-H4, Ub-H5, Ub-H6, Ub-H7 and Ub-H8, respectively.

Example 3

Expression and Purification of a Fusion Protein

In order to overexpress a fusion protein using the vector manufactured in Example 2, the fusion protein was expressed in *E. coli* BL21 (DE3) transformed with the vector (a vector encoding a fusion protein to which ubiquitin was attached). Then, a YT medium was used as a culture medium, to which 0.1 mM of IPTG was added when the optical density (O.D.) value was 0.5 at 600 nm, and the cells were incubated at 18° C. for another 16 hrs. The cells obtained from the culture were sonicated in 50 mM Tris-HCl buffer (pH 7.4), and then centrifuged at 13,000 rpm to obtain a supernatant. The supernatant was applied to a $Ni^{2+}$-NTA superflow column (Qiagen) equilibrated with the buffer and washed with a washing buffer (50 mM Tris-HCl, pH 7.4, 1 M NaCl) corresponding to 5 times of the column volume, and the protein was eluted with an elution buffer (50 mM Tris-HCl, pH 7.4, 250 mM Imidazole). Fractions including the fusion protein were collected, applied to a Q column (Amersham Biosciences) equilibrated with the buffer (50 mM Tris-HCl, pH 7.4, 250 mM Imidazole) and washed with a cleaning buffer (50 mM Tris-HCl, pH 7.4) corresponding to 5 times of the column volume, and the protein was eluted with an elution buffer (50 mM Tris-HCl, pH 7.4, 500 mM NaCl). Fractions including the fusion protein were collected and a dialysis was performed to remove salts. The protein was concentrated using Amicon (Millipore). The concentration of the purified protein was measured by using BSA as a standard. Using SDS-PAGE, the fusion protein (Ub-H2) was identified as approximately 30 kDa and purified (see FIG. 3).

A pharmaceutical composition including a fusion protein consisting of a first protein comprising a polypeptide which specifically binds to Annexin A1 and a second protein comprising a polypeptide which induces a cytotoxic activity of a cytotoxic lymphocyte linked to the end of the first protein; and a pharmaceutically acceptable carrier according to an embodiment may effectively prevent or treat cancer.

Example 4

Cell Culture, Cell Lines and T-Cell Isolation

The human Burkitt's lymphoma cells Ramos were purchased from the American Type Culture Collection (ATCC CRL-1596). Gastric cancer cell lines SNU1 and SNU5 were purchased from the American Type Culture Collection (ATCC CRL-5971 and ATCC CRL-5973). Cells were cultured as recommended by the supplier.

Peripheral blood mononuclear cells (PBMC) were isolated by Ficoll-Paque density gradient centrifugation from blood obtained from local blood banks Red blood cells (RBC) were removed by incubation in RBC lysis buffer (155 mM NH4Cl, 10 mM KHCO3, and 0.1 mM EDTA) for 15 min at room temperature. The cells were precipitated by centrifugation (5 minutes at 600 g). The supernatant was discarded, and cells were resuspended in PBS. Afterwards, the bulk of thrombocytes was removed by centrifugation for 15 min at 110 g.

PBMC were resuspended in culture medium and typically used up to 4 days after preparation without stimulation. CD8+ T cells were isolated using the Human CD8 Subset Column kit (R&D Systems, Wiesbaden, Germany).

Example 5

Cytotoxicity Assay

A calcein AM release assay was used for the determination of the cytotoxic activity of Annexin A1 binding peptide fused with CD3 (AA1BPxCD3). Cytotoxic T cell clones (generated from PMBC) were mixed with target cells (Ramos, SNU-1, or SNU-2 prepared in Example 4) and incubated for 3 hr at various concentrations of AA1BPxCD3 at an effector-to-target (E:T) ratio of 10:1. Cytotoxicity was determined after 3 hr.

Specifically, Ramos or SNU-5 or SNU-1 cells ($1.5 \times 10^7$) were labeled with 10 mM calcein AM (Molecular Probes) for 30 min at 37° C. in cell culture medium. After 3 washes in cell culture medium, cell density was adjusted to $3 \times 10^5$ cells/mL in RPMI 1640/10% FCS and 100 μL aliquots of $3 \times 10^4$ cells were used per assay reaction.

Figure 3:
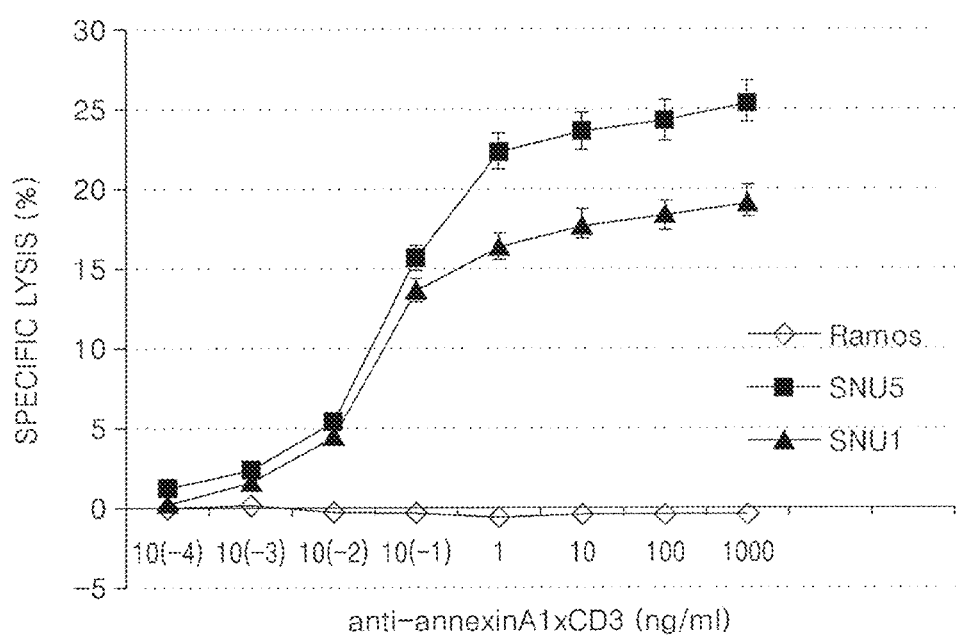
FIG. 3 is a graph illustrating the effect of AA1BPxCD3-activated T cells on isolated annexin A1—positive/—negative cells. Specific lysis (%) is indicated on the y-axis and anti-annexin A1xCD3 (ng/mL) is indicated on the x-axis. Mean values from triplicate determinations of specific target lysis in percent are shown.

In a 96-well round-bottom plate, CD8+ T cells and target cells were co-cultured at various AA1BPxCD3 concentrations in triplicate (see FIG. 3). For the E:T ratios of 10:1, the number of target cells was kept constant at $3 \times 10^4$ cells/well. AA1BPxCD3 was diluted in RPMI 1640/10% FCS to the required concentration. In a total reaction volume of 200 μL; the reactions were incubated for 3 hr. Fluorescent calcein released from lysed cells was measured using a fluorescence reader (2104 EnVision® Multilabel Reader, USA). Control fluorescent calcein was determined by incubating effector and target cells in the absence of AA1BPxCD3.

To determine total cell lysis, the mixture of effector and labeled target cells without AA1BPxCD3 was lysed by the addition of 20 μL of 1% saponin for 10 min. Specific cytotoxicity was calculated according to the following formula:

% spec.lysis=[(fluorescene of sample−fluorescene of control)/(fluorescene of total lysis−fluorescene of control)]×100

Mean values from triplicate determinations of specific target lysis in percent are shown in FIG. 3.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A fusion protein comprising:
   (a) a polypeptide that binds to Annexin A1 selected from the group consisting of SEQ ID NOs: 1-42, and
   (b) an anti-CD3 antibody or an antigen binding fragment thereof.

2. The fusion protein of claim 1, wherein the fusion protein further comprises a linker which links (a) and (b).

3. The fusion protein of claim 1, wherein the anti-CD3 antibody or antigen binding fragment comprises the amino acid sequence of SEQ ID NO: 116 or SEQ ID NO: 117.

* * * * *

SEQUENCE LISTING

```
<160> NUMBER OF SEQ ID NOS: 122

<210> SEQ ID NO 1
<211> LENGTH: 7
<212> TYPE: PRT
<213> ORGANISM: Artificial Sequence
<220> FEATURE:
<223> OTHER INFORMATION: Sythetic
<220> FEATURE:
<221> NAME/KEY: MISC_FEATURE
<223> OTHER INFORMATION: polypeptide binding specifically to Annexin A1

<400> SEQUENCE: 1

Gln Trp Gly His Thr Leu Trp
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: polypeptide binding specifically to Annexin A1

<400> SEQUENCE: 2

Lys Trp Gly His Glu Val Trp
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: polypeptide binding specifically to Annexin
      A1MISC_FEATURE

<400> SEQUENCE: 3

Trp Trp Gly His Glu Gln Trp
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: polypeptide binding specifically to Annexin A1

<400> SEQUENCE: 4

Pro Trp Gly His Glu Ile Trp
1               5
```

```
<210> SEQ ID NO 5
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: polypeptide binding specifically to Annexin A1

<400> SEQUENCE: 5

Leu Trp Gly His His Ile Trp
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: polypeptide binding specifically to Annexin A1

<400> SEQUENCE: 6

Leu Trp Gly His Gln Ile Trp
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: polypeptide binding specifically to Annexin A1

<400> SEQUENCE: 7

Leu Trp Gly His Gly Met Trp
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: polypeptide binding specifically to Annexin A1

<400> SEQUENCE: 8

Ala Trp Gly His Pro Phe Trp
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 9

Met Asn Arg Val
1
```

```
<210> SEQ ID NO 10
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 10

Ser Leu Asn Ser Ile Leu
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 11

Asn Leu Asn Ala Trp Phe
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 12

Val Glu Trp Pro Trp Trp
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 13

Trp Leu Trp Pro Arg Leu
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 14

Ile Asp Tyr Gly Leu Phe
```

```
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 15

Val Glu Gly Gln Gln Trp Trp
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 16

Trp Met Gly His Ser Ala Trp
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 17

Gly Ile His His Pro Ile Trp
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 18

Trp Gly Gly His Pro Ile Trp
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 19
```

```
Pro Trp Ala Lys Ile Phe Trp
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 20

Met Gly Ser Lys Met Trp Gly
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 21

Met Leu Trp Glu Asp Gln Asp
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 22

Glu Leu Phe Asp Gly Tyr Asp
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 23

Trp Pro Trp Glu Ala Asn His
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 24
```

```
Glu Gln Tyr Gly Phe Pro Phe
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 25

Ser Gly Phe Gly His Met Ile Trp
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 26

Glu Thr Arg Phe His Ala Ile Trp
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 27

Met Leu His His His Gln Arg Glu
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 28

Ala Leu His Asn Glu Pro His Thr
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1
```

```
<400> SEQUENCE: 29

Ala Phe His Asn Asp Pro Ala Glu
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 30

Leu Leu Phe Ser Asp Ile Gly Asn
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 31

Leu Val Leu Lys Gly Lys Trp His
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 32

Ser Gly Asn Gly Lys Pro Phe Trp Met
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 33

Ile Gln Arg Gly Gly Val Asp Trp Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1
```

```
<400> SEQUENCE: 34

Arg Asp Ser Gln Ser Trp Ser Trp Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 35

Leu Leu Glu Ser Gln Asn Pro Gln Asp
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 36

Ile Ile Asn Gly Trp Asn Pro Ile Trp
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 37

Asp Trp Thr Thr Ala Tyr Gly Pro Ser
1               5

<210> SEQ ID NO 38
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 38

Ile Tyr Asp Gly Asn Trp Ser Tyr Trp His
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
```

<223> OTHER INFORMATION: polypeptide binding specifically to Annexin A1

<400> SEQUENCE: 39

Ser Thr Asp Ser Asn Trp Phe Phe Asn Ala
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 40

Met Pro Glu Asn Trp Ile Ser Trp Tyr Arg
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 41

Val Arg Thr Asp Trp Tyr Ser Met Leu Met
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide binding specifically to Annexin A1

<400> SEQUENCE: 42

Met Ile Gln Thr Ser Ser Ala Asn Arg Asp
1               5                   10

<210> SEQ ID NO 43
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 43
cagtggggcc atacccctgtg g                                           21

<210> SEQ ID NO 44
<211> LENGTH: 21
<212> TYPE: DNA
<213> ORGANISM: Artificial Sequence
<220> FEATURE:
<223> OTHER INFORMATION: Synthetic
<220> FEATURE:

<221> NAME/KEY: misc_feature
<223> OTHER INFORMATION: polynucleotide encoding polypeptide binding
      specifically to Annexin A1

<400> SEQUENCE: 44
aaatggggcc atgaagtgtg g                                              21

<210> SEQ ID NO 45
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 45
tggtggggcc atgaacagtg g                                              21

<210> SEQ ID NO 46
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 46
ccgtggggcc atgaaatttg g                                              21

<210> SEQ ID NO 47
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 47
ctgtggggcc atcatatttg g                                              21

<210> SEQ ID NO 48
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 48
ctgtggggcc atcagatttg g                                              21

<210> SEQ ID NO 49
<211> LENGTH: 21
<212> TYPE: DNA
<213> ORGANISM: Artificial Sequence
<220> FEATURE:
<223> OTHER INFORMATION: Synthetic

```
<220> FEATURE:
<221> NAME/KEY: misc_feature
<223> OTHER INFORMATION: polynucleotide encoding polypeptide binding
      specifically to Annexin A1

<400> SEQUENCE: 49
ctgtggggcc atggcatgtg g                                            21

<210> SEQ ID NO 50
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 50
gcgtggggcc atccgttttg g                                            21

<210> SEQ ID NO 51
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 51
atgaaccgcg tg                                                      12

<210> SEQ ID NO 52
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 52
agcctgaaca gcattctg                                                18

<210> SEQ ID NO 53
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 53
aacctgaacg cgtggttt                                                18

<210> SEQ ID NO 54
<211> LENGTH: 18
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 54
gtggaatggc cgtggtgg                                                  18

<210> SEQ ID NO 55
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 55
tggctgtggc cgcgcctg                                                  18

<210> SEQ ID NO 56
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 56
attgattatg gcctgtttt                                                 18

<210> SEQ ID NO 57
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 57
gtggaaggcc agcagtggtg g                                              21

<210> SEQ ID NO 58
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 58
tggatgggcc atagcgcgtg g                                              21

<210> SEQ ID NO 59
<211> LENGTH: 21
<212> TYPE: DNA
<213> ORGANISM: Artificial Sequence
```

<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 59
ggcattcatc atccgatttg g                                             21

<210> SEQ ID NO 60
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 60
tggggcggcc atccgatttg g                                             21

<210> SEQ ID NO 61
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 61
ccgtgggcga aaattttttg g                                             21

<210> SEQ ID NO 62
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 62
atgggcagca aaatgtgggg c                                             21

<210> SEQ ID NO 63
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 63
atgctgtggg aagatcagga t                                             21

<210> SEQ ID NO 64
<211> LENGTH: 21
<212> TYPE: DNA

<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 64
gaactgtttg atggctatga t                                              21

<210> SEQ ID NO 65
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 65
tggccgtggg aagcgaacca t                                              21

<210> SEQ ID NO 66
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 66
gaacagtatg gctttccgtt t                                              21

<210> SEQ ID NO 67
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 67
agcggctttg gccatatgat ttgg                                           24

<210> SEQ ID NO 68
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 68
gaaacccgct ttcatgcgat ttgg                                           24

<210> SEQ ID NO 69
<211> LENGTH: 24

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 69
atgctgcatc atcatcagcg cgaa                                            24

<210> SEQ ID NO 70
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 70
gcgctgcata acgaaccgca tacc                                            24

<210> SEQ ID NO 71
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 71
gcgtttcata acgatccggc ggaa                                            24

<210> SEQ ID NO 72
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 72
ctgctgttta gcgatattgg caac                                            24

<210> SEQ ID NO 73
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 73
ctggtgctga aaggcaaatg gcat                                            24

<210> SEQ ID NO 74
```

```
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 74
agcggcaacg gcaaaccgtt ttggatg                                             27

<210> SEQ ID NO 75
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 75
attcagcgcg gcggcgtgga ttggagc                                             27

<210> SEQ ID NO 76
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 76
cgcgatagcc agagctggag ctggagc                                             27

<210> SEQ ID NO 77
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 77
ctgctggaaa gccagaaccc gcaggat                                             27

<210> SEQ ID NO 78
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 78
attattaacg gctggaaccc gatttgg                                             27
```

```
<210> SEQ ID NO 79
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 79
gattggacca ccgcgtatgg cccgagc                                           27

<210> SEQ ID NO 80
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 80
atttatgatg gcaactggag ctattggcat                                        30

<210> SEQ ID NO 81
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 81
agcaccgata gcaactggtt ttttaacgcg                                        30

<210> SEQ ID NO 82
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 82
atgccggaaa actggattag ctggtatcgc                                        30

<210> SEQ ID NO 83
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 83
gtgcgcaccg attggtatag catgctgatg                                        30
```

<210> SEQ ID NO 84
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding polypeptide binding
      specifically to Annexin A1

<400> SEQUENCE: 84
atgattcaga ccagcagcgc gaaccgcgat                                    30

<210> SEQ ID NO 85
<211> LENGTH: 894
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding fusion protein
      including mouse anti-CD3 and AWGHPFW
<220> FEATURE:
<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(454)
<223> OTHER INFORMATION: mouse anti-CD3 VH
<220> FEATURE:
<221> NAME/KEY: misc_feature
<222> LOCATION: (455)..(508)
<223> OTHER INFORMATION: Linker between VH and VL
<220> FEATURE:
<221> NAME/KEY: misc_feature
<222> LOCATION: (509)..(826)
<223> OTHER INFORMATION: mouse anti-CD3 VL
<220> FEATURE:
<221> NAME/KEY: misc_feature
<222> LOCATION: (827)..(841)
<223> OTHER INFORMATION: (GGGGS) linker
<220> FEATURE:
<221> NAME/KEY: misc_feature
<222> LOCATION: (842)..(868)
<223> OTHER INFORMATION: peptide sequence AWGHPFW

<400> SEQUENCE: 85
atggctagca aatacctgct gccgaccgct gctgctggtc tgctgctcct cgctgcccag      60
ccggcgatgg ccgactacaa agatgatgac gataaggata tcaaactgca gcagtcaggg     120
gctgaactgg caagacctgg ggcctcagtg aagatgtcct gcaagacttc tggctacacc     180
tttactaggt acacgatgca ctgggtaaaa cagaggcctg acagggtct ggaatggatt      240 ggatacatta atcctagccg tggttatact aattacaatc agaagttcaa ggacaaggcc     300
acattgacta cagacaaatc ctccagcaca gcctacatgc aactgagcag cctgacatct     360
gaggactctg cagtctatta ctgtgcaaga tattatgatg atcattactg ccttgactac     420
tggggccaag gcaccactct cacagtctcc tcagtcgaag gtggaagtgg aggttctggt     480
ggaagtggag gttcaggtgg agtcgacgac attcagctga cccagtctcc agcaatcatg     540
tctgcatctc caggggagaa ggtcaccatg acctgcagag ccagttcaag tgtaagttac     600
atgaactggt accagcagaa gtcaggcacc tcccccaaaa gatggattta tgacacatcc     660

```
aaagtggctt ctggagtccc ttatcgcttc agtggcagtg ggtctgggac ctcatactct    720
ctcacaatca gcagcatgga ggctgaagat gctgccactt attactgcca acagtggagt    780
agtaacccgc tcacgttcgg tgctgggacc aagctggagc tgaaaggagg tggtggatcc    840
tgcgcgtggg gccatccgtt ttggtgcctc gagcaccacc accaccacca ctga          894
```

<210> SEQ ID NO 86
<211> LENGTH: 894
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding fusion protein
  including mouse anti-CD3 and LWGHHIW
<220> FEATURE:
<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(454)
<223> OTHER INFORMATION: mouse anti-CD3 VH
<220> FEATURE:
<221> NAME/KEY: misc_feature
<222> LOCATION: (455)..(508)
<223> OTHER INFORMATION: Linker between VH and VL
<220> FEATURE:
<221> NAME/KEY: misc_feature
<222> LOCATION: (509)..(826)
<223> OTHER INFORMATION: mouse anti-CD3 VL
<220> FEATURE:
<221> NAME/KEY: misc_feature
<222> LOCATION: (827)..(841)
<223> OTHER INFORMATION: (GGGGS) linker
<220> FEATURE:
<221> NAME/KEY: misc_feature
<222> LOCATION: (842)..(868)
<223> OTHER INFORMATION: peptide sequence LWGHHIW

<400> SEQUENCE: 86

```
atggctagca ataccctgct gccgaccgct gctgctggtc tgctgctcct cgctgcccag    60
ccggcgatgg ccgactacaa agatgatgac gataaggata tcaaactgca gcagtcaggg    120
gctgaactgg caagacctgg ggcctcagtg aagatgtcct gcaagacttc tggctacacc    180
tttactaggt acacgatgca ctgggtaaaa cagaggcctg acagggtct ggaatggatt    240 ggatacatta atcctagccg tggttatact aattacaatc agaagttcaa ggacaaggcc    300
acattgacta cagacaaatc ctccagcaca gcctacatgc aactgagcag cctgacatct    360
gaggactctg cagtctatta ctgtgcaaga tattatgatg atcattactg ccttgactac    420
tggggccaag gcaccactct cacagtctcc tcagtcgaag gtggaagtgg aggttctggt    480
ggaagtggag gttcaggtgg agtcgacgac attcagctga cccagtctcc agcaatcatg    540
tctgcatctc caggggagaa ggtcaccatg acctgcagag ccagttcaag tgtaagttac    600
atgaactggt accagcagaa gtcaggcacc tcccccaaaa gatggattta tgacacatcc    660
aaagtggctt ctggagtccc ttatcgcttc agtggcagtg ggtctgggac ctcatactct    720
ctcacaatca gcagcatgga ggctgaagat gctgccactt attactgcca acagtggagt    780
agtaacccgc tcacgttcgg tgctgggacc aagctggagc tgaaaggagg tggtggatcc    840
```

-continued tgcctgtggg gccatcatat ttggtgcctc gagcaccacc accaccacca ctga    894

<210> SEQ ID NO 87
<211> LENGTH: 894
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding fusion protein
      including mouse anti-CD3 and MLWEDQD
<220> FEATURE:
<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(454)
<223> OTHER INFORMATION: mouse anti-CD3 VH
<220> FEATURE:
<221> NAME/KEY: misc_feature
<222> LOCATION: (455)..(508)
<223> OTHER INFORMATION: Linker between VH and VL
<220> FEATURE:
<221> NAME/KEY: misc_feature
<222> LOCATION: (509)..(826)
<223> OTHER INFORMATION: mouse anti-CD3 VL
<220> FEATURE:
<221> NAME/KEY: misc_feature
<222> LOCATION: (827)..(841)
<223> OTHER INFORMATION: (GGGGS) linker
<220> FEATURE:
<221> NAME/KEY: misc_feature
<222> LOCATION: (842)..(868)
<223> OTHER INFORMATION: peptide sequence MLWEDQD

<400> SEQUENCE: 87
atggctagca ataccgctgct gccgaccgct gctgctggtc tgctgctcct cgctgcccag    60
ccggcgatgg ccgactacaa agatgatgac gataaggata tcaaactgca gcagtcaggg    120
gctgaactgg caagacctgg ggcctcagtg aagatgtcct gcaagacttc tggctacacc    180
tttactaggt acacgatgca ctgggtaaaa cagaggcctg acagggtct ggaatggatt    240 ggatacatta atcctagccg tggttatact aattacaatc agaagttcaa ggacaaggcc    300
acattgacta cagacaaatc ctccagcaca gcctacatgc aactgagcag cctgacatct    360
gaggactctg cagtctatta ctgtgcaaga tattatgatg atcattactg ccttgactac    420
tggggccaag gcaccactct cacagtctcc tcagtcgaag gtggaagtgg aggttctggt    480
ggaagtggag gttcaggtgg agtcgacgac attcagctga cccagtctcc agcaatcatg    540
tctgcatctc cagggggagaa ggtcaccatg acctgcagag ccagttcaag tgtaagttac    600
atgaactggt accagcagaa gtcaggcacc tcccccaaaa gatggattta tgacacatcc    660
aaagtggctt ctggagtccc ttatcgcttc agtggcagtg gtctgggac ctcatactct    720 ctcacaatca gcagcatgga ggctgaagat gctgccactt attactgcca acagtggagt    780
agtaacccgc tcacgttcgg tgctgggacc aagctggagc tgaaaggagg tggtggatcc    840
tgcatgctgt gggaagatca ggattgcctc gagcaccacc accaccacca ctga    894

<210> SEQ ID NO 88
<211> LENGTH: 894
<212> TYPE: DNA
<213> ORGANISM: Artificial Sequence

```
<220> FEATURE:
<223> OTHER INFORMATION: Synthetic
<220> FEATURE:
<221> NAME/KEY: misc_feature
<223> OTHER INFORMATION: polynucleotide encoding fusion protein
      including mouse anti-CD3 and PWAKIFW
<220> FEATURE:
<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(454)
<223> OTHER INFORMATION: mouse anti-CD3 VH
<220> FEATURE:
<221> NAME/KEY: misc_feature
<222> LOCATION: (455)..(508)
<223> OTHER INFORMATION: Linker between VH and VL
<220> FEATURE:
<221> NAME/KEY: misc_feature
<222> LOCATION: (509)..(826)
<223> OTHER INFORMATION: mouse anti-CD3 VL
<220> FEATURE:
<221> NAME/KEY: misc_feature
<222> LOCATION: (827)..(841)
<223> OTHER INFORMATION: (GGGGS) linker
<220> FEATURE:
<221> NAME/KEY: misc_feature
<222> LOCATION: (842)..(868)
<223> OTHER INFORMATION: peptide sequence PWAKIFW

<400> SEQUENCE: 88
atggctagca aatacctgct gccgaccgct gctgctggtc tgctgctcct cgctgcccag      60
ccggcgatgg ccgactacaa agatgatgac gataaggata tcaaactgca gcagtcaggg     120
gctgaactgg caagacctgg ggcctcagtg aagatgtcct gcaagacttc tggctacacc     180
tttactaggt acacgatgca ctgggtaaaa cagaggcctg acagggtct ggaatggatt      240 ggatacatta atcctagccg tggttatact aattacaatc agaagttcaa ggacaaggcc     300
acattgacta cagacaaatc ctccagcaca gcctacatgc aactgagcag cctgacatct     360
gaggactctg cagtctatta ctgtgcaaga tattatgatg atcattactg ccttgactac     420
tggggccaag caccactct cacagtctcc tcagtcgaag gtggaagtgg aggttctggt      480
ggaagtggag gttcaggtgg agtcgacgac attcagctga cccagtctcc agcaatcatg     540
tctgcatctc cagggagaa ggtcaccatg acctgcagag ccagttcaag tgtaagttac     600
atgaactggt accagcagaa gtcaggcacc tcccccaaaa gatggattta tgacacatcc     660
aaagtggctt ctggagtccc ttatcgcttc agtggcagtg gtctgggac ctcatactct      720 ctcacaatca gcagcatgga ggctgaagat gctgccactt attactgcca acagtggagt     780
agtaacccgc tcacgttcgg tgctgggacc aagctggagc tgaaaggagg tggtggatcc     840
tgcccgtggg cgaaaatttt ttggtgcctc gagcaccacc accaccacca ctga           894

<210> SEQ ID NO 89
<211> LENGTH: 894
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding fusion protein
      including mouse anti-CD3 and PWGHEIW
<220> FEATURE:
```

<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(454)
<223> OTHER INFORMATION: mouse anti-CD3 VH
<220> FEATURE:
<221> NAME/KEY: misc_feature
<222> LOCATION: (455)..(508)
<223> OTHER INFORMATION: Linker between VH and VL
<220> FEATURE:
<221> NAME/KEY: misc_feature
<222> LOCATION: (509)..(826)
<223> OTHER INFORMATION: mouse anti-CD3 VL
<220> FEATURE:
<221> NAME/KEY: misc_feature
<222> LOCATION: (827)..(841)
<223> OTHER INFORMATION: (GGGGS) linker
<220> FEATURE:
<221> NAME/KEY: misc_feature
<222> LOCATION: (842)..(868)
<223> OTHER INFORMATION: peptide sequence PWGHEIW

<400> SEQUENCE: 89

```
atggctagca aatacctgct gccgaccgct gctgctggtc tgctgctcct cgctgcccag      60
ccggcgatgg ccgactacaa agatgatgac gataaggata tcaaactgca gcagtcaggg     120
gctgaactgg caagacctgg ggcctcagtg aagatgtcct gcaagacttc tggctacacc     180
tttactaggt acacgatgca ctgggtaaaa cagaggcctg acagggtct ggaatggatt      240
ggatacatta tcctagccg tggttatact aattacaatc agaagttcaa ggacaaggcc      300
acattgacta cagacaaatc ctccagcaca gcctacatgc aactgagcag cctgacatct     360
gaggactctg cagtctatta ctgtgcaaga tattatgatg atcattactg ccttgactac     420
tggggccaag gcaccactct cacagtctcc tcagtcgaag gtggaagtgg aggttctggt     480
ggaagtggag gttcaggtgg agtcgacgac attcagctga cccagtctcc agcaatcatg     540
tctgcatctc caggggagaa ggtcaccatg acctgcagag ccagttcaag tgtaagttac     600
atgaactggt accagcagaa gtcaggcacc tcccccaaaa gatggattta tgacacatcc     660
aaagtggctt ctggagtccc ttatcgcttc agtggcagtg gtctgggac ctcatactct      720
ctcacaatca gcagcatgga ggctgaagat gctgccactt attactgcca acagtggagt     780
agtaacccgc tcacgttcgg tgctgggacc aagctggagc tgaaaggagg tggtggatcc     840
tgcccgtggg gtcatgaaat tggtgcctc gagcaccacc accaccacca ctga            894
```

<210> SEQ ID NO 90
<211> LENGTH: 894
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding fusion protein
      including mouse anti-CD3 and QWGHTLW
<220> FEATURE:
<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(454)
<223> OTHER INFORMATION: mouse anti-CD3 VH
<220> FEATURE:
<221> NAME/KEY: misc_feature
<222> LOCATION: (455)..(508)
<223> OTHER INFORMATION: Linker between VH and VL
<220> FEATURE:
<221> NAME/KEY: misc_feature
<222> LOCATION: (509)..(826)
<223> OTHER INFORMATION: mouse anti-CD3 VL
<220> FEATURE:
<221> NAME/KEY: misc_feature
<222> LOCATION: (827)..(841)
<223> OTHER INFORMATION: (GGGGS) linker
<220> FEATURE:
<221> NAME/KEY: misc_feature
<222> LOCATION: (842)..(868)
<223> OTHER INFORMATION: peptide sequence QWGHTLW

<400> SEQUENCE: 90

| | | |
|---|---|---|
| atggctagca aatacctgct gccgaccgct gctgctggtc tgctgctcct cgctgcccag | 60 |
| ccggcgatgg ccgactacaa agatgatgac gataaggata tcaaactgca gcagtcaggg | 120 |
| gctgaactgg caagacctgg ggcctcagtg aagatgtcct gcaagacttc tggctacacc | 180 |
| tttactaggt acacgatgca ctgggtaaaa cagaggcctg acagggtct ggaatggatt | 240 |
| ggatacatta atcctagccg tggttatact aattacaatc agaagttcaa ggacaaggcc | 300 |
| acattgacta cagacaaatc ctccagcaca gcctacatgc aactgagcag cctgacatct | 360 |
| gaggactctg cagtctatta ctgtgcaaga tattatgatg atcattactg ccttgactac | 420 |
| tggggccaag gcaccactct cacagtctcc tcagtcgaag gtggaagtgg aggttctggt | 480 |
| ggaagtggag gttcaggtgg agtcgacgac attcagctga cccagtctcc agcaatcatg | 540 |
| tctgcatctc caggggagaa ggtcaccatg acctgcagag ccagttcaag tgtaagttac | 600 |
| atgaactggt accagcagaa gtcaggcacc tcccccaaaa gatggattta tgacacatcc | 660 |
| aaagtggctt ctggagtccc ttatcgcttc agtggcagtg gtctgggac ctcatactct | 720 |
| ctcacaatca gcagcatgga ggctgaagat gctgccactt attactgcca acagtggagt | 780 |
| agtaacccgc tcacgttcgg tgctgggacc aagctggagc tgaaaggagg tggtggatcc | 840 |
| tgccagtggg gtcataccct gtggtgcctc gagcaccacc accaccacca ctga | 894 |

<210> SEQ ID NO 91
<211> LENGTH: 894
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding fusion protein
    including mouse anti-CD3 and VEGQQWW
<220> FEATURE:
<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(454)
<223> OTHER INFORMATION: mouse anti-CD3 VH
<220> FEATURE:
<221> NAME/KEY: misc_feature
<222> LOCATION: (455)..(508)

```
<223> OTHER INFORMATION: Linker between VH and VL
<220> FEATURE:
<221> NAME/KEY: misc_feature
<222> LOCATION: (509)..(826)
<223> OTHER INFORMATION:  ouse anti-CD3 VL
<220> FEATURE:
<221> NAME/KEY: misc_feature
<222> LOCATION: (827)..(841)
<223> OTHER INFORMATION: (GGGGS) linker
<220> FEATURE:
<221> NAME/KEY: misc_feature
<222> LOCATION: (842)..(868)
<223> OTHER INFORMATION: peptide sequence VEGQQWW

<400> SEQUENCE: 91
atggctagca aatacctgct gccgaccgct gctgctggtc tgctgctcct cgctgcccag      60
ccggcgatgg ccgactacaa agatgatgac gataaggata tcaaactgca gcagtcaggg     120
gctgaactgg caagacctgg ggcctcagtg aagatgtcct gcaagacttc tggctacacc     180
tttactaggt acacgatgca ctgggtaaaa cagaggcctg gacagggtct ggaatggatt     240
ggatacatta atcctagccg tggttatact aattacaatc agaagttcaa ggacaaggcc     300
acattgacta cagacaaatc ctccagcaca gcctacatgc aactgagcag cctgacatct     360
gaggactctg cagtctatta ctgtgcaaga tattatgatg atcattactg ccttgactac     420
tggggccaag gcaccactct cacagtctcc tcagtcgaag gtggaagtgg aggttctggt     480
ggaagtggag gttcaggtgg agtcgacgac attcagctga cccagtctcc agcaatcatg     540
tctgcatctc caggggagaa ggtcaccatg acctgcagag ccagttcaag tgtaagttac     600
atgaactggt accagcagaa gtcaggcacc tcccccaaaa gatggattta tgacacatcc     660
aaagtggctt ctggagtccc ttatcgcttc agtggcagtg ggtctgggac ctcatactct     720
ctcacaatca gcagcatgga ggctgaagat gctgccactt attactgcca acagtggagt     780
agtaacccgc tcacgttcgg tgctgggacc aagctggagc tgaaaggagg tggtggatcc     840
tgcgtggaag ccagcagtg gtggtgcctc gagcaccacc accaccacca ctga     894
```

<210> SEQ ID NO 92
<211> LENGTH: 894
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding fusion protein
      including mouse anti-CD3 and WMGHSAW
<220> FEATURE:
<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(454)
<223> OTHER INFORMATION: mouse anti-CD3 VH
<220> FEATURE:
<221> NAME/KEY: misc_feature
<222> LOCATION: (455)..(508)
<223> OTHER INFORMATION: Linker between VH and VL
<220> FEATURE:
<221> NAME/KEY: misc_feature
<222> LOCATION: (509)..(826)
<223> OTHER INFORMATION: mouse anti-CD3 VL
<220> FEATURE:
<221> NAME/KEY: misc_feature
<222> LOCATION: (827)..(841)
<223> OTHER INFORMATION: (GGGGS) linker
<220> FEATURE:
<221> NAME/KEY: misc_feature
<222> LOCATION: (842)..(868)
<223> OTHER INFORMATION: peptide sequence WMGHSAW

<400> SEQUENCE: 92

```
atggctagca aatacctgct gccgaccgct gctgctggtc tgctgctcct cgctgcccag      60
ccggcgatgg ccgactacaa agatgatgac gataaggata tcaaactgca gcagtcaggg     120
gctgaactgg caagacctgg ggcctcagtg aagatgtcct gcaagacttc tggctacacc     180
tttactaggt acacgatgca ctgggtaaaa cagaggcctg acagggtct ggaatggatt      240
ggatacatta atcctagccg tggttatact aattacaatc agaagttcaa ggacaaggcc     300
acattgacta cagacaaatc ctccagcaca gcctacatgc aactgagcag cctgacatct     360
gaggactctg cagtctatta ctgtgcaaga tattatgatg atcattactg ccttgactac     420
tggggccaag gcaccactct cacagtctcc tcagtcgaag gtggaagtgg aggttctggt     480
ggaagtggag gttcaggtgg agtcgacgac attcagctga cccagtctcc agcaatcatg     540
tctgcatctc caggggagaa ggtcaccatg acctgcagag ccagttcaag tgtaagttac     600
atgaactggt accagcagaa gtcaggcacc tcccccaaaa gatggattta tgacacatcc     660
aaagtggctt ctggagtccc ttatcgcttc agtggcagtg ggtctgggac ctcatactct     720
ctcacaatca gcagcatgga ggctgaagat gctgccactt attactgcca acagtggagt     780
agtaacccgc tcacgttcgg tgctgggacc aagctggagc tgaaaggagg tggtggatcc     840
tgctggatgg ccattccgc gtggtgcctc gagcaccacc accaccacca ctga            894
```

<210> SEQ ID NO 93
<211> LENGTH: 909
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding fusion protein
      including human anti-CD3 and AWGHPFW
<220> FEATURE:
<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(475)
<223> OTHER INFORMATION: human anti-CD3 VH
<220> FEATURE:
<221> NAME/KEY: misc_feature
<222> LOCATION: (476)..(520)
<223> OTHER INFORMATION: Linker between VH and VL
<220> FEATURE:
<221> NAME/KEY: misc_feature
<222> LOCATION: (521)..(841)
<223> OTHER INFORMATION: human anti-CD3 VL
<220> FEATURE:
<221> NAME/KEY: misc_feature
<222> LOCATION: (842)..(856)
<223> OTHER INFORMATION: (GGGGS) linker
<220> FEATURE:
<221> NAME/KEY: misc_feature
<222> LOCATION: (857)..(883)
<223> OTHER INFORMATION: peptide sequence AWGHPFW

<400> SEQUENCE: 93

```
atggctagca ataccctgct gccgaccgct gctgctggtc tgctgctcct cgctgcccag    60
ccggcgatgg ccgactacaa agatgatgac gataaggagc tgcagctggt cgagtggggc   120
gcaggactgt tgaagccttc ggagaccctg tccctcacct cgctgtctta tggtgggtcc   180
ttcagtggtt actactggag ctggatccgc cagcccccag ggaaggggct ggagtggatt   240
ggggaaatca atcatagtgg aagcaccaac tacaacccgt ccctcaagag tcgagtcacc   300
atatcagtag acacgtccaa gaaccagttc tccctgaagc tgagctctgt gaccgccgcg   360
gacacggctg tgtattactg tgcgagaggc cgaggccgat ttttggggtg gttattaggg   420
ggctccaact ggttcgaccc ctggggccag ggaaccctgg tcaccgtctc ctcaggtggt   480
ggtggttctg gcggcggcgg ctccggtggt ggtggttctg agctcgtgat gacccagtct   540
ccatcctccc tgtctgcatc tgtaggagac agagtcacca tcacttgccg ggcgagtcag   600
ggcattagca attatttaaa ttggtatcag cagaaaccag ggaaagcccc taagctcctg   660
atctacgatg catccaattt ggaaacaggg gtcccatcaa ggttcagtgg cagtggatct   720
gggacagatt tcactctcac catcagcagt ctgcaacctg aagattttgc aacttactac   780
tgtcaacaga gttacagtac cccgtacact tttggccagg ggaccaaagt ggatatcaaa   840
ggaggtggtg gatcctgcgc gtggggccat ccgttttggt gcctcgagca ccaccaccac   900
caccactga                                                            909
```

<210> SEQ ID NO 94
<211> LENGTH: 909
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding fusion protein
      including human anti-CD3 and LWGHHIW
<220> FEATURE:
<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(475)
<223> OTHER INFORMATION: human anti-CD3 VH
<220> FEATURE:
<221> NAME/KEY: misc_feature
<222> LOCATION: (476)..(520)
<223> OTHER INFORMATION: Linker between VH and VL
<220> FEATURE:
<221> NAME/KEY: misc_feature
<222> LOCATION: (521)..(841)
<223> OTHER INFORMATION: human anti-CD3 VL
<220> FEATURE:
<221> NAME/KEY: misc_feature
<222> LOCATION: (842)..(856)
<223> OTHER INFORMATION: (GGGGS) linker
<220> FEATURE:
<221> NAME/KEY: misc_feature
<222> LOCATION: (857)..(883)
<223> OTHER INFORMATION: peptide sequence LWGHHIW

<400> SEQUENCE: 94

```
atggctagca ataccctgct gccgaccgct gctgctggtc tgctgctcct cgctgcccag    60
ccggcgatgg ccgactacaa agatgatgac gataaggagc tgcagctggt cgagtggggc   120
```

```
gcaggactgt tgaagccttc ggagaccctg tccctcacct gcgctgtcta tggtgggtcc      180
ttcagtggtt actactggag ctggatccgc cagcccccag gaaggggct ggagtggatt       240 ggggaaatca atcatagtgg aagcaccaac tacaacccgt ccctcaagag tcgagtcacc      300
atatcagtag acacgtccaa gaaccagttc tccctgaagc tgagctctgt gaccgccgcg      360
gacacggctg tgtattactg tgcgagaggc cgaggccgat ttttggggtg gttattaggg      420
ggctccaact ggttcgaccc ctggggccag ggaaccctgg tcaccgtctc ctcaggtggt      480
ggtggttctg gcggcggcgg ctccggtggt ggtggttctg agctcgtgat gacccagtct      540
ccatcctccc tgtctgcatc tgtaggagac agagtcacca tcacttgccg ggcgagtcag      600
ggcattagca attatttaaa ttggtatcag cagaaaccag ggaaagcccc taagctcctg      660
atctacgatg catccaattt ggaaacaggg gtcccatcaa ggttcagtgg cagtggatct      720
gggacagatt tcactctcac catcagcagt ctgcaacctg aagattttgc aacttactac      780
tgtcaacaga gttacagtac cccgtacact tttggccagg ggaccaaagt ggatatcaaa      840
ggaggtggtg gatcctgcct gtggggccat catatttggt gcctcgagca ccaccaccac      900
caccactga                                                             909
```

<210> SEQ ID NO 95
<211> LENGTH: 909
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding fusion protein
      including human anti-CD3 and MLWEDQD
<220> FEATURE:
<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(475)
<223> OTHER INFORMATION: human anti-CD3 VH
<220> FEATURE:
<221> NAME/KEY: misc_feature
<222> LOCATION: (476)..(520)
<223> OTHER INFORMATION: Linker between VH and VL
<220> FEATURE:
<221> NAME/KEY: misc_feature
<222> LOCATION: (521)..(841)
<223> OTHER INFORMATION: human anti-CD3 VL
<220> FEATURE:
<221> NAME/KEY: misc_feature
<222> LOCATION: (842)..(856)
<223> OTHER INFORMATION: (GGGGS) linker
<220> FEATURE:
<221> NAME/KEY: misc_feature
<222> LOCATION: (857)..(883)
<223> OTHER INFORMATION: peptide sequence MLWEDQD

<400> SEQUENCE: 95

```
atggctagca aatacctgct gccgaccgct gctgctggtc tgctgctcct cgctgcccag       60
ccggcgatgg ccgactacaa agatgatgac gataaggagc tgcagctggt cgagtggggc      120
gcaggactgt tgaagccttc ggagaccctg tccctcacct gcgctgtcta tggtgggtcc      180
ttcagtggtt actactggag ctggatccgc cagcccccag gaaggggct ggagtggatt       240
```

```
ggggaaatca atcatagtgg aagcaccaac tacaacccgt ccctcaagag tcgagtcacc      300
atatcagtag acacgtccaa gaaccagttc ccctgaagc tgagctctgt gaccgccgcg       360
gacacggctg tgtattactg tgcgagaggc cgaggccgat ttttggggtg gttattaggg      420
ggctccaact ggttcgaccc ctggggccag ggaaccctgg tcaccgtctc ctcaggtggt      480
ggtggttctg gcggcggcgg ctccggtggt ggtggttctg agctcgtgat gacccagtct      540
ccatcctccc tgtctgcatc tgtaggagac agagtcacca tcacttgccg ggcgagtcag      600
ggcattagca attatttaaa ttggtatcag cagaaaccag ggaaagcccc taagctcctg      660
atctacgatg catccaattt ggaaacaggg gtcccatcaa ggttcagtgg cagtggatct      720
gggacagatt tcactctcac catcagcagt ctgcaacctg aagattttgc aacttactac      780
tgtcaacaga gttacagtac cccgtacact tttggccagg ggaccaaagt ggatatcaaa      840
ggaggtggtg gatcctgcat gctgtgggaa gatcaggatt gcctcgagca ccaccaccac      900
caccactga                                                              909

<210> SEQ ID NO 96
<211> LENGTH: 909
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding fusion protein
      including human anti-CD3 and PWAKIFW
<220> FEATURE:
<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(475)
<223> OTHER INFORMATION: human anti-CD3 VH
<220> FEATURE:
<221> NAME/KEY: misc_feature
<222> LOCATION: (476)..(520)
<223> OTHER INFORMATION: Linker between VH and VL
<220> FEATURE:
<221> NAME/KEY: misc_feature
<222> LOCATION: (521)..(841)
<223> OTHER INFORMATION: human anti-CD3 VL
<220> FEATURE:
<221> NAME/KEY: misc_feature
<222> LOCATION: (842)..(856)
<223> OTHER INFORMATION: (GGGGS) linker
<220> FEATURE:
<221> NAME/KEY: misc_feature
<222> LOCATION: (857)..(883)
<223> OTHER INFORMATION: peptide sequence PWAKIFW

<400> SEQUENCE: 96
atggctagca atacctgct gccgaccgct gctgctggtc tgctgctcct cgctgcccag       60
ccggcgatgg ccgactacaa agatgatgac gataaggagc tgcagctggt cgagtggggc     120
gcaggactgt tgaagccttc ggagaccctg tccctcacct cgctgtctca tgtgggtcc      180 ttcagtggtt actactggag ctggatccgc cagcccccag ggaagggct ggagtggatt      240 ggggaaatca atcatagtgg aagcaccaac tacaacccgt ccctcaagag tcgagtcacc     300
atatcagtag acacgtccaa gaaccagttc ccctgaagc tgagctctgt gaccgccgcg      360
gacacggctg tgtattactg tgcgagaggc cgaggccgat ttttggggtg gttattaggg     420
```

```
ggctccaact ggttcgaccc ctggggccag ggaaccctgg tcaccgtctc ctcaggtggt    480
ggtggttctg gcggcggcgg ctccggtggt ggtggttctg agctcgtgat gacccagtct    540
ccatcctccc tgtctgcatc tgtaggagac agagtcacca tcacttgccg ggcgagtcag    600
ggcattagca attatttaaa ttggtatcag cagaaaccag ggaaagcccc taagctcctg    660
atctacgatg catccaattt ggaaacaggg gtcccatcaa ggttcagtgg cagtggatct    720
gggacagatt tcactctcac catcagcagt ctgcaacctg aagattttgc aacttactac    780
tgtcaacaga gttacagtac cccgtacact tttggccagg gaccaaagt ggatatcaaa    840 ggaggtggtg atcctgccc gtgggcgaaa attttttggt gcctcgagca ccaccaccac    900
caccactga                                                           909
```

<210> SEQ ID NO 97
<211> LENGTH: 909
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding fusion protein
      including human anti-CD3 and PWGHEIW
<220> FEATURE:
<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(475)
<223> OTHER INFORMATION: human anti-CD3 VH
<220> FEATURE:
<221> NAME/KEY: misc_feature
<222> LOCATION: (476)..(520)
<223> OTHER INFORMATION: Linker between VH and VL
<220> FEATURE:
<221> NAME/KEY: misc_feature
<222> LOCATION: (521)..(841)
<223> OTHER INFORMATION: human anti-CD3 VL
<220> FEATURE:
<221> NAME/KEY: misc_feature
<222> LOCATION: (842)..(856)
<223> OTHER INFORMATION: (GGGGS) linker
<220> FEATURE:
<221> NAME/KEY: misc_feature
<222> LOCATION: (857)..(883)
<223> OTHER INFORMATION: peptide sequence PWGHEIW
<400> SEQUENCE: 97

```
atggctagca ataccctgct gccgaccgct gctgctggtc tgctgctcct cgctgcccag     60
ccggcgatgg ccgactacaa agatgatgac gataaggagc tgcagctggt cgagtggggc    120
gcaggactgt tgaagccttc ggagaccctg tccctcacct cgctgtgcta tggtgggtcc    180
ttcagtggtt actactggag ctggatccgc cagcccccag ggaaggggct ggagtggatt    240
ggggaaatca atcatagtgg aagcaccaac tacaacccgt ccctcaagag tcgagtcacc    300
atatcagtag acacgtccaa gaaccagttc tccctgaagc tgagctctgt gaccgccgcg    360
gacacggctg tgtattactg tgcgagaggc cgaggccgat ttttggggtg gttattaggg    420
ggctccaact ggttcgaccc ctggggccag ggaaccctgg tcaccgtctc ctcaggtggt    480
ggtggttctg gcggcggcgg ctccggtggt ggtggttctg agctcgtgat gacccagtct    540
```

| | |
|---|---:|
| ccatcctccc tgtctgcatc tgtaggagac agagtcacca tcacttgccg ggcgagtcag | 600 |
| ggcattagca attatttaaa ttggtatcag cagaaaccag ggaaagcccc taagctcctg | 660 |
| atctacgatg catccaattt ggaaacaggg gtcccatcaa ggttcagtgg cagtggatct | 720 |
| gggacagatt tcactctcac catcagcagt ctgcaacctg aagattttgc aacttactac | 780 |
| tgtcaacaga gttacagtac cccgtacact tttggccagg ggaccaaagt ggatatcaaa | 840 |
| ggaggtggtg gatcctgccc gtggggtcat gaaatttggt gcctcgagca ccaccaccac | 900 |
| caccactga | 909 |

```
<210> SEQ ID NO 98
<211> LENGTH: 909
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding fusion protein
      including human anti-CD3 and QWGHTLW
<220> FEATURE:
<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(475)
<223> OTHER INFORMATION: human anti-CD3 VH
<220> FEATURE:
<221> NAME/KEY: misc_feature
<222> LOCATION: (476)..(520)
<223> OTHER INFORMATION: Linker between VH and VL
<220> FEATURE:
<221> NAME/KEY: misc_feature
<222> LOCATION: (521)..(841)
<223> OTHER INFORMATION: human anti-CD3 VL
<220> FEATURE:
<221> NAME/KEY: misc_feature
<222> LOCATION: (842)..(856)
<223> OTHER INFORMATION: (GGGGS) linker
<220> FEATURE:
<221> NAME/KEY: misc_feature
<222> LOCATION: (857)..(883)
<223> OTHER INFORMATION: peptide sequence QWGHTLW
```

<400> SEQUENCE: 98

| | |
|---|---:|
| atggctagca ataccctgct gccgaccgct gctgctggtc tgctgctcct cgctgcccag | 60 |
| ccggcgatgg ccgactacaa agatgatgac gataaggagc tgcagctggt cgagtggggc | 120 |
| gcaggactgt tgaagccttc ggagaccctg tccctcacct cgctgtgtcta tggtgggtcc | 180 |
| ttcagtggtt actactggag ctggatccgc cagcccccag ggaaggggct ggagtggatt | 240 |
| gggaaaatca tcatagtgg aagcaccaac tacaacccgt ccctcaagag tcgagtcacc | 300 |
| atatcagtag acacgtccaa gaaccagttc tccctgaagc tgagctctgt gaccgccgcg | 360 |
| gacacggctg tgtattactg tgcgagaggc cgaggccgat ttttggggtg gttattaggg | 420 |
| ggctccaact ggttcgaccc ctggggccag ggaaccctgg tcaccgtctc ctcaggtggt | 480 |
| ggtggttctg gcggcggcgg ctccggtggt ggtggttctg agctcgtgat gacccagtct | 540 |
| ccatcctccc tgtctgcatc tgtaggagac agagtcacca tcacttgccg ggcgagtcag | 600 |
| ggcattagca attatttaaa ttggtatcag cagaaaccag ggaaagcccc taagctcctg | 660 |
| atctacgatg catccaattt ggaaacaggg gtcccatcaa ggttcagtgg cagtggatct | 720 |

| gggacagatt tcactctcac catcagcagt ctgcaacctg aagatttgc aacttactac | 780 |
| tgtcaacaga gttacagtac cccgtacact tttggccagg ggaccaaagt ggatatcaaa | 840 |
| ggaggtggtg gatcctgcca gtggggtcat accctgtggt gcctcgagca ccaccaccac | 900 |
| caccactga | 909 |

<210> SEQ ID NO 99
<211> LENGTH: 909
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding fusion protein
   including human anti-CD3 and VEGQQWW
<220> FEATURE:
<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(475)
<223> OTHER INFORMATION: human anti-CD3 VH
<220> FEATURE:
<221> NAME/KEY: misc_feature
<222> LOCATION: (476)..(520)
<223> OTHER INFORMATION: Linker between VH and VL
<220> FEATURE:
<221> NAME/KEY: misc_feature
<222> LOCATION: (521)..(841)
<223> OTHER INFORMATION: human anti-CD3 VL
<220> FEATURE:
<221> NAME/KEY: misc_feature
<222> LOCATION: (842)..(856)
<223> OTHER INFORMATION: (GGGGS) linker
<220> FEATURE:
<221> NAME/KEY: misc_feature
<222> LOCATION: (857)..(883)
<223> OTHER INFORMATION: peptide sequence VEGQQWW

<400> SEQUENCE: 99

| atggctagca aatacctgct gccgaccgct gctgctggtc tgctgctcct cgctgcccag | 60 |
| ccggcgatgg ccgactacaa agatgatgac gataaggagc tgcagctggt cgagtggggc | 120 |
| gcaggactgt tgaagccttc ggagaccctg tccctcacct gcgctgtcta tggtgggtcc | 180 |
| ttcagtggtt actactggag ctggatccgc cagcccccag gaagggggct ggagtggatt | 240 |
| ggggaaatca tcatagtgg aagcaccaac tacaacccgt ccctcaagag tcgagtcacc | 300 |
| atatcagtag acacgtccaa gaaccagttc tccctgaagc tgagctctgt gaccgccgcg | 360 |
| gacacggctg tgtattactg tgcgagaggc cgaggccgat ttttggggtg gttattaggg | 420 |
| ggctccaact ggttcgaccc ctggggccag ggaaccctgg tcaccgtctc ctcaggtggt | 480 |
| ggtggttctg gcggcggcgg ctccggtggt ggtggttctg agctcgtgat gacccagtct | 540 |
| ccatcctccc tgtctgcatc tgtaggagac agagtcacca tcacttgccg ggcgagtcag | 600 |
| ggcattagca attatttaaa ttggtatcag cagaaaccag ggaaagcccc taagctcctg | 660 |
| atctacgatg catccaattt ggaaacaggg gtcccatcaa ggttcagtgg cagtggatct | 720 |
| gggacagatt tcactctcac catcagcagt ctgcaacctg aagatttgc aacttactac | 780 |
| tgtcaacaga gttacagtac cccgtacact tttggccagg ggaccaaagt ggatatcaaa | 840 |

```
ggaggtggtg gatcctgcgt ggaaggccag cagtggtggt gcctcgagca ccaccaccac      900
caccactga                                                              909
```

<210> SEQ ID NO 100
<211> LENGTH: 909
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding fusion protein
      including human anti-CD3 and WMGHSAW
<220> FEATURE:
<221> NAME/KEY: misc_feature
<222> LOCATION: (11)..(73)
<223> OTHER INFORMATION: pelB: periplasmic signal sequence
<220> FEATURE:
<221> NAME/KEY: misc_feature
<222> LOCATION: (74)..(97)
<223> OTHER INFORMATION: FLAG
<220> FEATURE:
<221> NAME/KEY: misc_feature
<222> LOCATION: (98)..(475)
<223> OTHER INFORMATION: human anti-CD3 VH
<220> FEATURE:
<221> NAME/KEY: misc_feature
<222> LOCATION: (476)..(520)
<223> OTHER INFORMATION: Linker between VH and VL
<220> FEATURE:
<221> NAME/KEY: misc_feature
<222> LOCATION: (521)..(841)
<223> OTHER INFORMATION: human anti-CD3 VL
<220> FEATURE:
<221> NAME/KEY: misc_feature
<222> LOCATION: (842)..(856)
<223> OTHER INFORMATION: (GGGGS) linker
<220> FEATURE:
<221> NAME/KEY: misc_feature
<222> LOCATION: (857)..(883)
<223> OTHER INFORMATION: peptide sequence WMGHSAW

<400> SEQUENCE: 100

```
atggctagca aatacctgct gccgaccgct gctgctggtc tgctgctcct cgctgcccag       60
ccggcgatgg ccgactacaa agatgatgac gataaggagc tgcagctggt cgagtggggc      120
gcaggactgt tgaagccttc ggagaccctg tccctcacct gcgctgtcta tggtgggtcc      180
ttcagtggtt actactggag ctggatccgc cagcccccag gaagggggct ggagtggatt      240
ggggaaatca atcatagtgg aagcaccaac tacaacccgt ccctcaagag tcgagtcacc      300
atatcagtag acacgtccaa gaaccagttc tccctgaagc tgagctctgt gaccgccgcg      360
gacacggctg tgtattactg tgcgagaggc cgaggccgat ttttggggtg gttattaggg      420
ggctccaact ggttcgaccc ctggggccag ggaaccctgg tcaccgtctc ctcaggtggt      480
ggtggttctg gcggcggcgg ctccggtggt ggtggttctg agctcgtgat gacccagtct      540
ccatcctccc tgtctgcatc tgtaggagac agagtcacca tcacttgccg ggcgagtcag      600
ggcattagca attatttaaa ttggtatcag cagaaaccag ggaaagcccc taagctcctg      660
atctacgatg catccaattt ggaaacaggg gtcccatcaa ggttcagtgg cagtggatct      720
gggacagatt tcactctcac catcagcagt ctgcaacctg aagattttgc aacttactac      780
tgtcaacaga gttacagtac cccgtacact tttggccagg gaccaaagt ggatatcaaa       840 ggaggtggtg gatcctgctg gatgggccat tccgcgtggt gcctcgagca ccaccaccac      900
caccactga                                                              909
```

<210> SEQ ID NO 101
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: pelB:NdeI-F primer

<400> SEQUENCE: 101
cgccatatga aatacctgct gccgaccgct g                               31

<210> SEQ ID NO 102
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: pelB-NcoI:BamHI-R primer

<400> SEQUENCE: 102
cccggatccg gccatggccg gctggg                                     26

<210> SEQ ID NO 103
<211> LENGTH: 228
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polynucleotide encoding ubiquitin

<400> SEQUENCE: 103
atgcagattt ttgtgaaaac cctgaccggc aaaaccatta ccctggaagt ggaaccgagc      60
gataccattg aaaacgtgaa agcgaaaatt caggataaag aaggcattcc gccggatcag     120
cagcgcctga ttttgcggg caaacagctg aagatggcc gcaccctgag cgattataac      180
attcagaaag aaagcaccct gcatctggtg ctgcgcctgc gcggcggc               228

<210> SEQ ID NO 104
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Flag-mouse_a-CD3:EcoRI-F primer

<400> SEQUENCE: 104
ccggaattcg actacaaaga tgatgacgat aaggatatca aac                  43

<210> SEQ ID NO 105
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Flag-human_a-CD3:EcoRI-F primer

<400> SEQUENCE: 105
ccggaattcg actacaaaga tgatgacgat aaggagctg                       39

<210> SEQ ID NO 106
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: pep1:XhoI-R primer

<400> SEQUENCE: 106
ccgctcgagg caccaaaacg gatgg                                    25

<210> SEQ ID NO 107
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: pep2:XhoI-R primer

<400> SEQUENCE: 107
ccgctcgagg caccaaatat gatggcc                                  27

<210> SEQ ID NO 108
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: pep3:XhoI-R primer

<400> SEQUENCE: 108
ccgctcgagg caatcctgat cttcccac                                 28

<210> SEQ ID NO 109
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: pep4:XhoI-R primer

<400> SEQUENCE: 109
ccgctcgagg caccaaaaaa ttttcgc                                  27

<210> SEQ ID NO 110
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: pep5:XhoI-R primer

<400> SEQUENCE: 110
ccgctcgagg caccaaattt catgacc                                  27

<210> SEQ ID NO 111
<211> LENGTH: 27

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: pep6:XhoI-R primer

<400> SEQUENCE: 111
ccgctcgagg caccacaggg tatgacc                                            27

<210> SEQ ID NO 112
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: pep7:XhoI-R primer

<400> SEQUENCE: 112
ccgctcgagg caccaccact gctgg                                              25

<210> SEQ ID NO 113
<211> LENGTH: 24
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: pep8:XhoI-R primer

<400> SEQUENCE: 113
ccgctcgagg caccacgcgg aatg                                               24

<210> SEQ ID NO 114
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: TN-forward primer

<400> SEQUENCE: 114
ggaggaagcg gccgcggtac tggcagc                                            27

<210> SEQ ID NO 115
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: TN-reverse primer

<400> SEQUENCE: 115
cctcctctct agagcggacc aggagc                                             26

<210> SEQ ID NO 116
<211> LENGTH: 243
<212> TYPE: PRT
<213> ORGANISM: Artificial Sequence
<220> FEATURE:
<223> OTHER INFORMATION: Synthetic
```

```
<220> FEATURE:
<221> NAME/KEY: misc_feature
<223> OTHER INFORMATION: anti-CD3 scFv antibody (mouse)

<400> SEQUENCE: 116
```

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Val Asp Asp Ile Gln Leu Tyr Gln Ser
    130                 135                 140

Pro Ala Thr Met Ser Ala Ser Pro Gly Glu Lys Val Thr Met Thr Cys
145                 150                 155                 160

Arg Ala Ser Ser Val Ser Tyr Met Asn Trp Tyr Gln Gln Lys Ser
            165                 170                 175

Gly Thr Ser Pro Lys Arg Trp Ile Tyr Asp Thr Ser Lys Val Ala Ser
        180                 185                 190

Gly Val Pro Tyr Arg Phe Ser Gly Ser Gly Ser Gly Thr Ser Tyr Ser
    195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys

```
<210> SEQ ID NO 117
<211> LENGTH: 248
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: anti-CD3 scFv antibody (human)

<400> SEQUENCE: 117
```

Glu Leu Gln Leu Val Glu Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu

```
                65                  70                  75                  80
Lys Leu Ser Ser Val Thr Ala Ala Asp Thr Ala Val Tyr Tyr Cys Ala
                    85                  90                  95

Arg Gly Arg Gly Arg Phe Leu Gly Trp Leu Gly Gly Ser Asn Trp
            100                 105                 110

Phe Asp Pro Trp Gly Gln Gly Thr Leu Val Thr Val Ser Gly Gly
        115                 120                 125

Gly Gly Ser Gly Gly Gly Ser Gly Gly Gly Ser Glu Leu Val
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Gly Ile Ser Asn Tyr Leu Asn Trp
                165                 170                 175

Tyr Gln Gln Lys Pro Gly Lys Ala Pro Lys Leu Leu Ile Tyr Asp Ala
            180                 185                 190

Ser Asn Leu Glu Thr Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Ser Tyr Ser Thr Pro Tyr Thr Phe Gly
225                 230                 235                 240

Gln Gly Thr Lys Val Asp Ile Lys
                245

<210> SEQ ID NO 118
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: endonexin-fold
<220> FEATURE:
<221> NAME/KEY: misc_feature
<222> LOCATION: (2)..(2)
<223> OTHER INFORMATION: Xaa is any Amino Acid

<400> SEQUENCE: 118

Gly Xaa Gly Thr Asp Glu
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: polypeptide specifically bind to Annexin A1
<220> FEATURE:
<221> NAME/KEY: misc_feature
<222> LOCATION: (1)..(1)
<223> OTHER INFORMATION: Xaa is an amino acid selected from the group
      consisting of Ala, Ile, Leu, Met, Phe, Pro, Trp, Val, Asn, Cys,
      Gln, Gly, Ser, Thr, Tyr, Asp, Glu, Arg, His, and Lys
<220> FEATURE:
<221> NAME/KEY: misc_feature
<222> LOCATION: (5)..(5)
<223> OTHER INFORMATION: Xaa is an amino acid selected from the group
      consisting of Ala, Ile, Leu, Met, Phe, Pro, Trp, Val, Asn, Cys,
      Gln, Gly, Ser, Thr, Tyr, Asp, Glu, Arg, His, and Lys
<220> FEATURE:
<221> NAME/KEY: misc_feature
```

```
<222> LOCATION: (6)..(6)
<223> OTHER INFORMATION: Xaa is an amino acid selected from the group
      consisting of Ala, Ile, Leu, Met, Phe, Pro, Trp, Val, Asn, Cys,
      Gln, Gly, Ser, Thr,
      and Tyr

<400> SEQUENCE: 119

Xaa Trp Gly His Xaa Xaa Trp
1               5

<210> SEQ ID NO 120
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: peptide linker

<400> SEQUENCE: 120

Gly Gly Gly Gly Ser
1               5

<210> SEQ ID NO 121
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: peptide linker

<400> SEQUENCE: 121

Gly Gly Gly Gly Ser Gly Gly Gly Gly Ser Gly Gly Gly Gly Ser
1               5                   10                  15

<210> SEQ ID NO 122
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: peptide linker

<400> SEQUENCE: 122

Gly Gly Gly Gly Ser Gly Gly Gly Gly Ser
1               5                   10
```